(12) United States Patent
Chakraborty et al.

(10) Patent No.: US 9,200,034 B2
(45) Date of Patent: Dec. 1, 2015

(54) OLIGOPEPTIDES AND PROCESS FOR PREPARATION THEREOF

(75) Inventors: Tushar Kanti Chakraborty, Lucknow (IN); Praveen Kumar Gajula, Lucknow (IN); Dulal Panda, Mumbai (IN); Jayant Asthana, Mumbai (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 0 days.

(21) Appl. No.: 14/005,202

(22) PCT Filed: Jan. 23, 2012

(86) PCT No.: PCT/IN2012/000051
§ 371 (c)(1),
(2), (4) Date: Sep. 13, 2013

(87) PCT Pub. No.: WO2012/123957
PCT Pub. Date: Sep. 20, 2012

(65) Prior Publication Data
US 2014/0005121 A1      Jan. 2, 2014

(30) Foreign Application Priority Data
Mar. 16, 2011   (IN) .............................. 732/DEL/2011

(51) Int. Cl.
*C07K 5/02* (2006.01)
*C07D 307/24* (2006.01)
*A61K 38/00* (2006.01)

(52) U.S. Cl.
CPC .............. *C07K 5/02* (2013.01); *C07D 307/24* (2013.01); *C07K 5/021* (2013.01); *C07K 5/0205* (2013.01); *A61K 38/00* (2013.01)

(58) Field of Classification Search
None
See application file for complete search history.

(56) References Cited

FOREIGN PATENT DOCUMENTS

WO   2006011000 A1   2/2006
WO   2006063707 A1   6/2006

OTHER PUBLICATIONS

Bai et al ('Structure-activity studies with chiral isomers and with segments of the antimitotic marine peptide dolastatin 10' Biochemical Pharmacology v40(8) 1990 pp. 1859-1864).*

English Language and Usage (retrieved from http://english.stackexchange.com/questions/7871/between-a-and-b-or-from-a-to-b on Dec. 22, 2014, 2 pages).*

Petel, Shreyaskumar, et al., Phase II Study of Intravenous TZT-1027 in Patients with Advanced or Metastitic Soft-Tissue Sarcomas with Prior Exposure to Anthracycline-Based Chemotherapy, American Cancer Society 107, 2006, p. 2881-2887.

Pettit, R. George, et al., Dolastatins 24, Synthesis of (-)-dolastatin 10.1 X-Ray molecular structure of N, N-dimethylvalyl-valyl-dolaisoleuine Tert-butyl ester, J. Chem. Soc., Perkin Trans. 1, 1996, p. 859-863.

* cited by examiner

*Primary Examiner* — James H Alstrum Acevedo
*Assistant Examiner* — Ronald Niebauer
(74) *Attorney, Agent, or Firm* — Blank Rome LLP

(57) ABSTRACT

This invention relates to oligopeptides having general formula (I). The invention also relates to the process of preparation thereof, wherein the said compounds are selective anti-cancer agents over a panel of human cancer cell lines. Further, this invention relates that said anti-cancer peptides are prepared by a novel method.

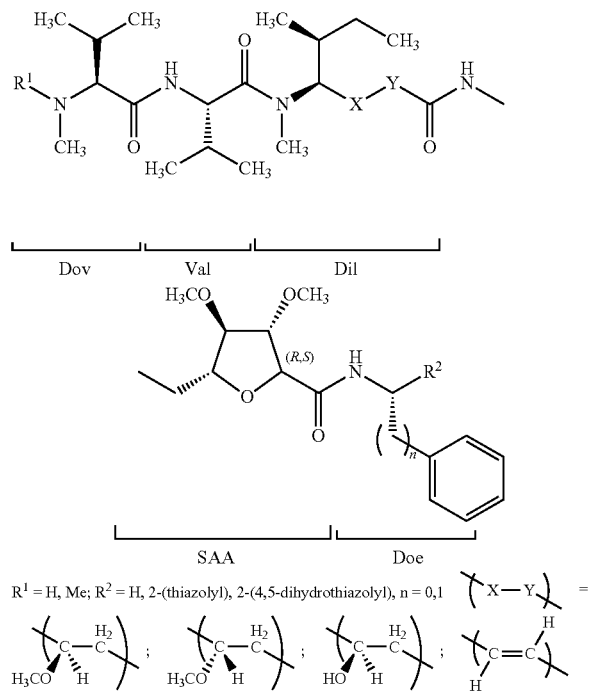

16 Claims, 13 Drawing Sheets

OLIGOPEPTIDES AND PROCESS FOR PREPARATION THEREOF

CROSS-REFERENCE TO RELATED APPLICATIONS

Figure 1:
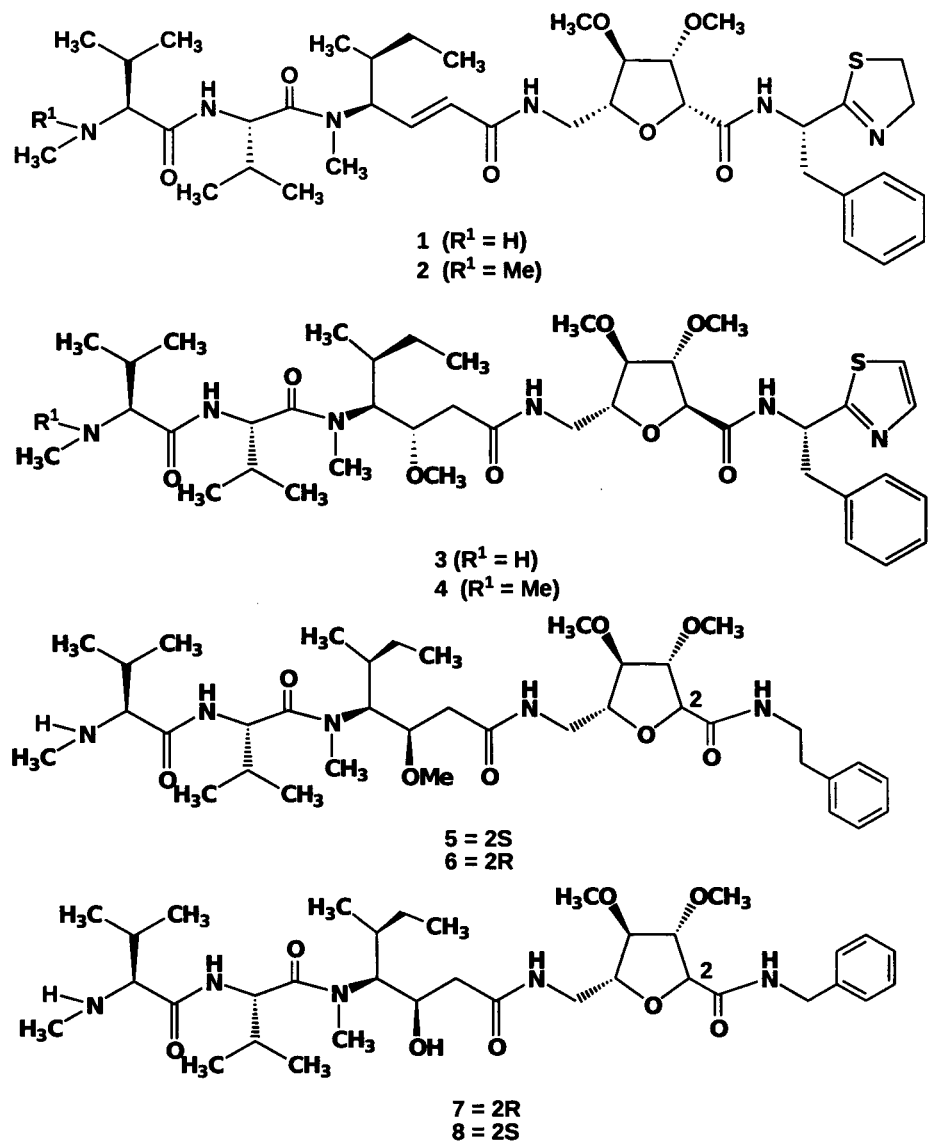

The present application is a national phase of International Patent Application No. PCT/IN2012/000051, filed Jan. 23, 2012, which claims priority to Indian Patent Application No. 0732/DEL/2011, filed Mar. 16, 2011, the entire disclosures of which are incorporated by reference herein.

FIELD OF THE INVENTION

The present invention relates to oligopeptides having general formula (I). The invention also relates to the process of preparation thereof, wherein the said compounds are selective anti-cancer agents over a panel of human cancer cell lines.

BACKGROUND OF THE INVENTION

Dolastatins have been isolated from a mollusk, *Dolabella auricularia*, (sea hare) from the Indian Ocean. The linear peptide Dolastatin-10 and the desipeptide Dolastatin-15 have shown most promising antiproliferative activities. Dolastatin-10 has a linear structure of 4 amino acids linked to a complex primary amine. Three of its amino acids (dolavaline, dolaisoleucine, and dolaproline) and its terminal amine (dolaphenine) are unique to the mollusk from which it was isolated. The inhibition of cell proliferation and induction of apoptosis in malignant cell lines by dolastatins are mediated through interactions with tubulin, resulting in the alteration of microtubule function. Dolastatins also exert cytotoxic effects in animals bearing intraperitoneal tumors. However, phase I and II clinical trials utilizing Dolastatin-10 did not demonstrate any responses in a variety of solid tumors and soft tissue sarcomas (Von Mehren et al, *Sarcoma* 2004; 8: 107). Dolastatin-15 showed severe side effects such as arterial hypertension and myocardial infarction. The low yields of chemical synthesis of dolastatins, together with their poor water solubility have motivated the synthesis and evaluation of new synthetic peptides. TZT-1027 is a synthetic tetrapeptide derivative of Dolastatin-10 with potent antitumor activity. It has a broader range of antitumor activity in vitro and in vivo against a variety of tumors including those that are taxane- and vincristine-resistant. Although some evidence of activity was observed in Phase I studies, no activity of TZT-1027 was observed in the Phase II trials (Patel et al, *Cancer* 2006; 107: 2881). Despite the side effects and toxicity, the mechanism of action of these molecules, make them attractive leads for developing new anti-cancer therapy, especially in combination with other anticancer drugs.

General Formula-I

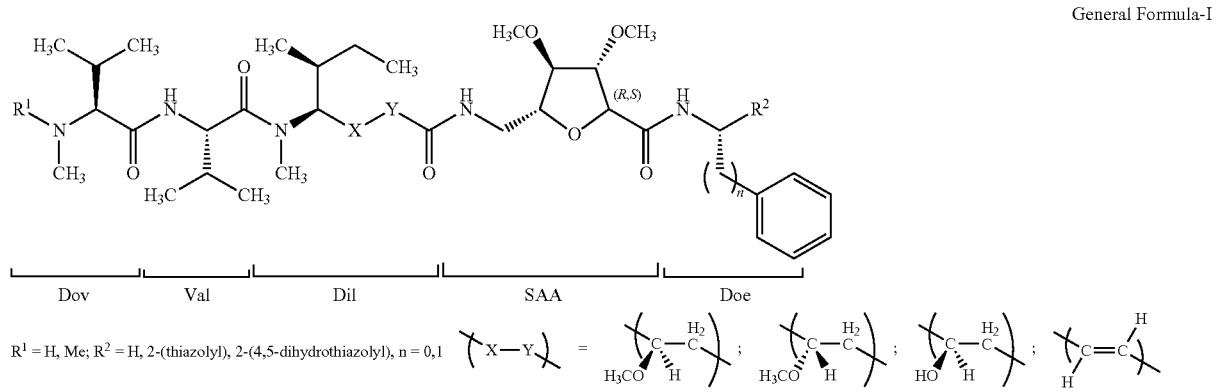

OBJECTS OF THE INVENTION

The main object of this invention is to provide novel peptide compounds of general formula (I), or its pharmaceutically acceptable salts as anticancer medicament.

Another object of this invention is to provide the said compounds of general formula (I) for the manufacture of medicament for the treatment of cervical carcinoma and breast carcinoma.

SUMMARY OF THE INVENTION

Accordingly, the present invention provides an oligopeptide of general formula (I) and pharmaceutical salts thereof:

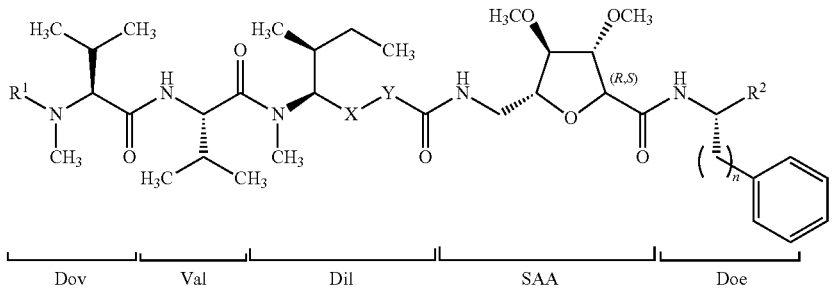

where in:
Dov=(S)-Dolavaline, wherein $R^1$ can be H, Me
Val=(S)-Valine
Dil=Dolaisoleucine, wherein X=C(OH)H, C(OCH$_3$), CH. and Y=CH$_2$, CH
SAA=Sugar Amino Acid, Wherein SAA can be 2R, 2S
Doe=(S)-Dolapheine, wherein $R^2$ can be H, 2-(thiazolyl), 2-(4,5-dihydrothiazolyl), and n=0.1

In an embodiment of the invention, the representative compounds of general formula (I) comprises:
(a) Dov($R^1$=H)-Val-(4S,5S)-Dil(X,Y=CH)-SAA(2R)-Doe($R^2$=2-(4,5-dihydrothiazolyl), n=1) (Compound 1);
(b) Dov($R^1$=Me)-Val-(4S,5S)-Dil(X,Y=CH)-SAA(2R)-Doe($R^2$=2-(4,5-dihydrothiazolyl), n=1) (Compound 2);
(c) Dov($R^1$=H)-Val-(3S,4S,5S)-Dil(X=C(OCH$_3$)H, Y=CH$_2$)-SAA(2S)-Doe($R^2$=2-(thiazolyl), n=1) (Compound 3);
(d) Dov($R^1$=Me)-Val-(3S,4S,5S)-Dil(X=C(OCH$_3$)H, Y=CH$_2$)-SAA(2S)-Doe($R^2$=2-(thiazolyl), n=1) (Compound 4);
(e) Dov($R^1$=H)-Val-(3R,4S,5S)-Dil(X=C(OCH$_3$)H, Y=CH$_2$)-SAA(2S)-Doe($R^2$=H, n=1) (Compound 5);
(f) Dov($R^1$=H)-Val-(3R,4S,5S)-Dil(X=C(OCH$_3$)H, Y=CH$_2$)-SAA(2R)-Doe($R^2$=H, n=1) (Compound 6);
(g) Dov($R^1$=H)-Val-(3R,4S,5S)-Dil(X=C(OH)H, Y=CH$_2$)-SAA(2R)-Doe($R^2$=H, n=0) (Compound 7);
(h) Dov($R^1$=H)-Val-(3R,4S,5S)-Dil(X=C(OH)H, Y=CH$_2$)-SAA(2S)-Doe($R^2$=H, n=0) (Compound 8).

In another embodiment of the invention, the representative compounds of general formula (I) comprises the following structures:

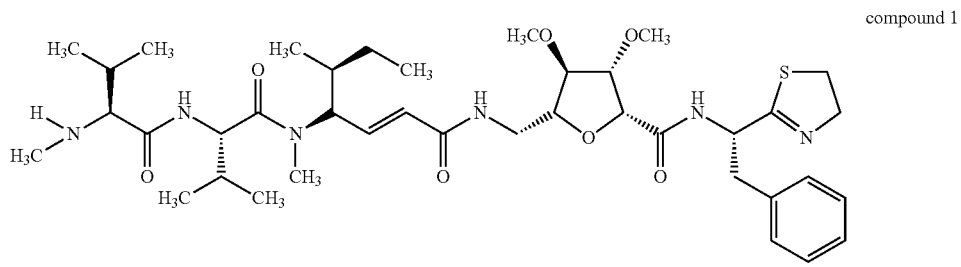

compound 1

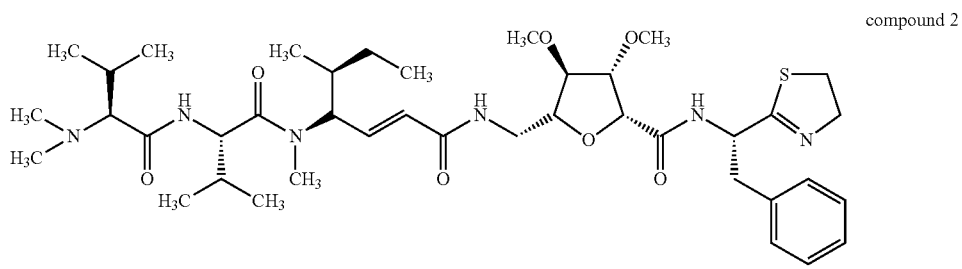

compound 2

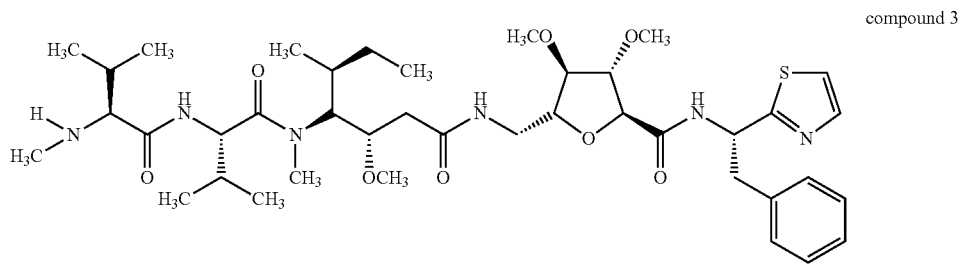

compound 3

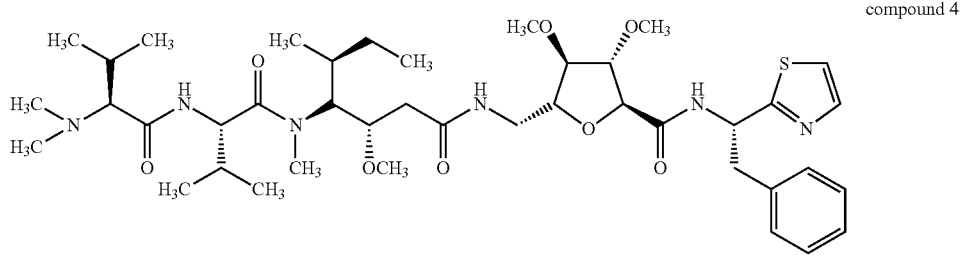

compound 4

-continued

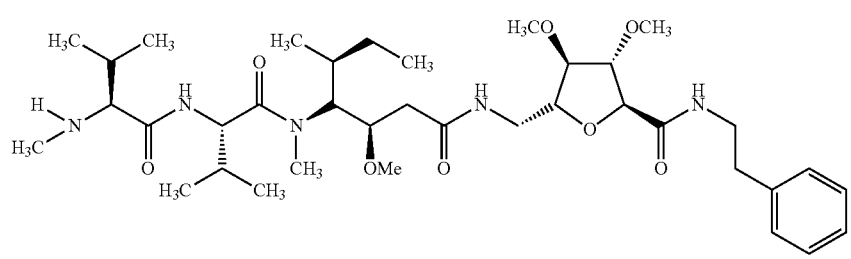

compound 5

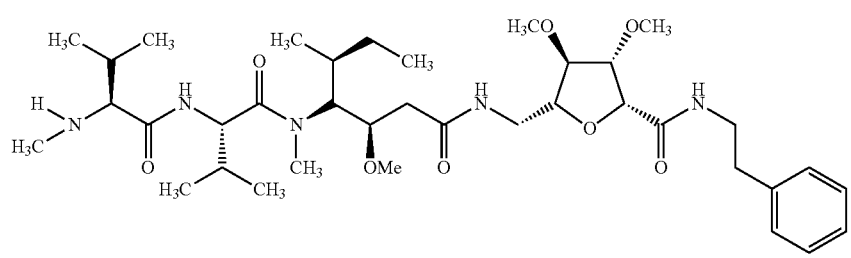

compound 6

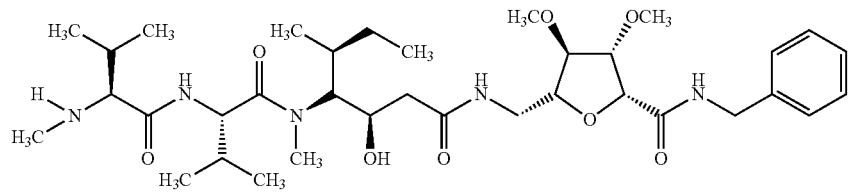

compound 7

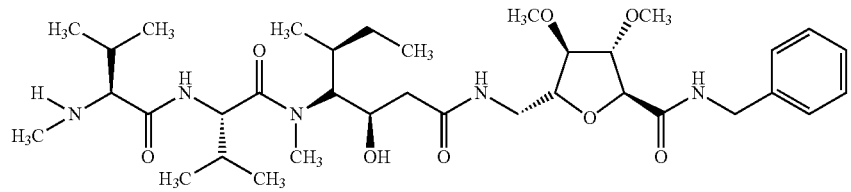

compound 8

Yet another embodiment of the invention is use of oligopeptide of general formula I in medicament for the treatment of cancers selected from the group consisting of breast carcinoma and cervical carcinoma.

In another embodiment of the invention, the compounds show $IC_{50}$ values ranging between 6.8 nM to 12 nM.

In yet another embodiment of the invention, the compound 5 causes apoptosis in 40 to 70% cells at a concentration in the range of 7 to 30 nM.

In yet another embodiment of the invention, the compounds showed inhibition of tubulin polymerization up to 50% at a concentration ranging from 5 to 6 nM.

In yet another embodiment of the invention, the compound 5 showed depolymerization of interphase and mitotic microtubules at 15 to 30 nM.

In yet another embodiment of the invention, the pharmaceutically acceptable salts are selected from acid addition salts formed from suitable non-toxic organic and inorganic acids.

In yet another embodiment of the invention, the acid addition salts are derived from inorganic acids selected from the group consisting of hydrochloric acid, hydrobromic acid, hydroiodic acid, sulfuric acid, phosphoric acid and nitric acid.

In yet another embodiment of the invention, the acid addition salts are derived from organic acids are selected from the group consisting of p-toluenesulfonic acid, naphthalenesulphonic acid, naphthalene disulphonic acid, methanesulphonic acid, ethanesulphonic acid and trifluoroacetic acid.

In yet another embodiment of the invention, the acid addition salts are derived from trifluoroacetic acid.

Another embodiment of the invention provides a process for the preparation of compound of the formula (I) comprising the steps of:

(i) reacting a compound selected from the group consisting of 9, 10 and 14 in a mixture of solvents THF/MeOH/H2O (3:1:1) with LiOH.H$_2$O and stirring the mixture at a temperature in the range of 0° C. to 30° C., acidifying the resulting reaction mixture with 1N HCl, extracting the reaction mixture with ethyl acetate, washing with water and brine and concentrating in vacuum to obtain acid 38 from 9, 23 from 10 or 30 from 14;

(ii) deprotecting of tert-Butyloxycarbonyl group by reacting the compound selected from a group consisting of 11, 12, and 17 in dichloromethane, with trifluoroacetic acid and stirring the mixture at a temperature in the range of 25° C. to 30° C., concentrating the reaction mixture under vacuum, followed by azeotroping with dichloromethane to obtain the trifluoroacetate salt 22, 37 or 47 from 11, 12 and 17 respectively;

(iii) coupling of an acid compound selected from the group consisting of 23, 29 and 38 obtained in step (i) with TFA salt selected from the group consisting of 22, 37 and 47 obtained in step (ii) and 21 by sequential addition of HOBt and EDCI and DIPEA until reaction mixture is basic in a solvent dichloromethane or DMF at a temperature in the range of 0° C. to 5° C., followed by stirring at 25° C. to 30°

C. for another period of 1 h to 12 h, diluting the the reaction mixture with a solvent followed by washing with 1N HCl solution, saturated NaHCO$_3$ solution, water and brine, concentrating and purifying by standard chromatographic techniques to obtain the dipetides of formulae 34, 41, 50, 56, 61 or 65;

(iv) deprotecting tert-Butyloxycarbonyl group of the dipeptides as obtained in step (iii) by the process as described in step (ii) to obtain trifluoroacetate salts 27, 29, 43, 52, 57, or 66;

(v) reacting the acid 20 in dichloromethane and pyridine with a solution of DAST in dichloromethane via cannula, and stirring at 25° C. to 30° C. for the time ranging between 30 min to 1 hr, diluting with CH$_2$Cl$_2$, washing with ice-cold water, concentrating to obtain acid fluoride 25;

(vi) deprotecting of tert-Butyloxycarbonyl group by the process as described in step (ii) by reacting the compound selected from a group consisting of compound 13, 15, and 16 to obtain the corresponding trifluoroacetate salts 24, 39 or 48;

(vii) coupling the acid fluoride 25 obtained in step (v) with deprotected amino acids selected from group of compounds obtained in step (vi) in the presence of DIPEA in a solvent dichloromethane or DMF at 0° C. to 5° C. followed by stirring at 25° C. to 30° C. for another period of 1 h to 12 h, diluting the reaction mixture with a solvent after stirring, washing with 1N HCl solution, saturated NaHCO$_3$ solution, water and brine, concentrating and purifying by standard chromatographic techniques to obtain the dipeptides 33, 40 or 49;

(viii) reacting the dipeptide compound selected from a the group obtained in step (vii), by the process as described in step (i) to obtain acids 26, 42 or 51;

(ix) coupling of an acid compound selected from group obtained in step (viii) with a trifluoroacetate salt selected from a group obtained in step (iv) by the process as described in step (iii) to obtain the tetrapetides 35, 44, 53 or 58;

(x) deprotection of tert-Butyloxycarbonyl group as described in step (ii) by reacting the tetrapeptide compounds selected from step (ix) to obtain the trifluoroacetate salts 28, 45, 54 or 59;

(xi) coupling of an acid compound selected from group obtained in step (i) with a trifluoroacetate salt selected from a group obtained in step (iv) by the process as described in step (iii) to obtain the tripeptides 30 or 62;

(xii) deprotecting of tert-Butyloxycarbonyl group by the process as described in step (ii) by reacting the compounds selected from the group consisting of tripeptide compounds obtained in step (xi) to obtain the trifluoroacetate salts 67 or 68;

(xiii) coupling of an acid compound 20 with a deprotected tripeptide selected from the group obtained in step (xii) by sequential addition of BOP-Cl and DIPEA until reaction mixture turns basic, in a solvent dichloromethane or DMF at 0° C. to 5° C. followed by stirring at 25° C. to 30° C. for another period of 1 h to 12 h, diluting the reaction mixture with a solvent after stirring, washing with 1N HCl solution, saturated NaHCO$_3$ solution, water and brine, and concentrating and purifying by standard chromatographic techniques to provide the tetrapetides 32 or 69;

(xiv) deprotecting of tert-Butyloxycarbonyl group by the process as described in step (ii) by reacting the compounds selected from the group consisting of tetrapeptide compounds obtained in step (xiii) to obtain the trifluoroacetate salts 63 or 70;

(xv) coupling of an acid selected from 18 or 19 with a deprotected tetrapeptide selected from the group obtained in step (x) and (xiv) by sequential addition of HOBt and EDCI and DIPEA until reaction mixture turns basic in a solvent dichloromethane or DMF at 0° C. to 5° C. followed by stirring at 25° C. to 30° C. for another period of 1 h to 12 h, diluting the reaction mixture with a solvent after stirring, washing with 1N HCl solution, saturated NaHCO$_3$ solution, water and brine, and concentrating and purifying by standard chromatographic techniques to obtain the Boc protected pentapetides 36, 46, 55, 60, 64 or 71 or compounds 2 or 4;

(xvi) deprotecting of tert-Butyloxycarbonyl protected pentapetides 36, 4.6, 55, 60, 64, 71 obtained in step (xv) with trifluoroacetic acid in dichloromethane, at a temperature ranging between 0° C. to 30° C., for a period in the range of 30 minutes to 60 minutes, the reaction mixture was then concentrated in vacuum, followed by azeotroping with dichloromethane to obtain the trifluoroacetate salts i.e., compounds 1, 3, 5, 6, 7 or 8.

In yet another embodiment of the invention, the solvent in step (ii) is selected from the group consisting of EtOAc, DCM, chloroform, and a mixture of methanol and chloroform in a ratio ranging between 0:10 and 1:10.

Another embodiment of the invention provides oligopeptides comprising the intermediate compounds of formula 34, 41, 50, 56, 61, 65, 27, 29, 43, 52, 57, 66, 35, 44, 53, 58, 28, 5, 54, 59, 30, 62, 67, 68, 32, 69, 63, 70, 36, 46, 55, 60, 64, 71.

Yet another embodiment of the invention provides a pharmaceutical composition comprising an effective amount of one or more of the compounds of formula (I), along with pharmaceutically acceptable excipients.

In yet another embodiment of the invention, the pharmaceutically acceptable excipients are selected from the group consisting of carriers, fillers, binders, disintegrating agents, lubricants, absorbents, wetting agents, buffering agents or a combination thereof.

In yet another embodiment of the invention, the carriers are selected from the group consisting of dicalcium phosphate and sodium citrate.

In yet another embodiment of the invention, the fillers are selected from the group consisting of mannitol, glucose, lactose and sucrose.

In yet another embodiment of the invention, the binders are selected from the group consisting of disaccharides, polysaccharides, sugar alcohols and polymers.

In yet another embodiment of the invention, the disaccharides are selected from the group consisting of sucrose and lactose, the polysaccharides are selected from the group consisting of starch and cellulose, the sugar alcohols are selected from the group consisting of sorbitol and the polymers are selected from the group consisting of polyvinyl pyrrolidinone.

In yet another embodiment of the invention, the disintegrating agents are selected from the group consisting of potato, silicates, agar-agar, and sodium carbonate.

In yet another embodiment of the invention, the lubricants are selected from the group consisting of silica, talc, magnesium stearate, sodium lauryl sulfate and stearic acid.

In yet another embodiment of the invention, the absorbents are selected from the group consisting of bentonite, fuller's earth and kaolin.

In yet another embodiment of the invention, the wetting agents are selected from the group consisting of glycerol monostearate and sodium lauryl sulphate.

BRIEF DESCRIPTION OF THE ACCOMPANYING DRAWINGS

FIG. 1: shows the structures of the new Anti-cancer Peptides 1-8.

Figure 2:
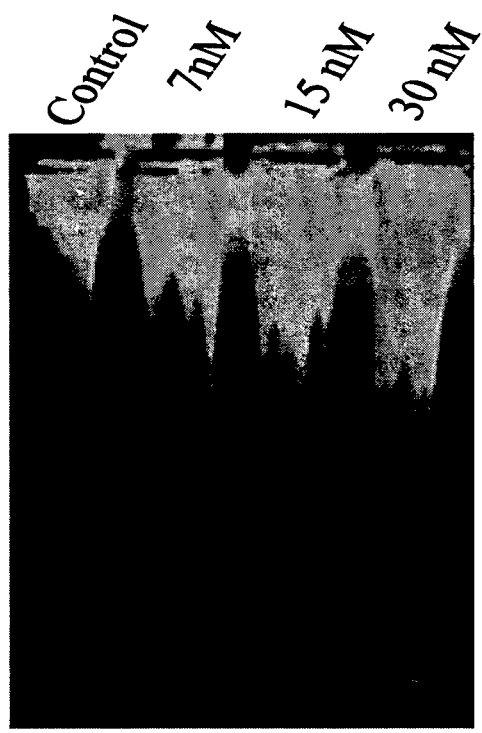

FIG. 2: shows DNA fragmentation caused by different concentrations of compound 5 (most potent among all 8 compounds). Untreated control is shown for reference.

Figure 3:
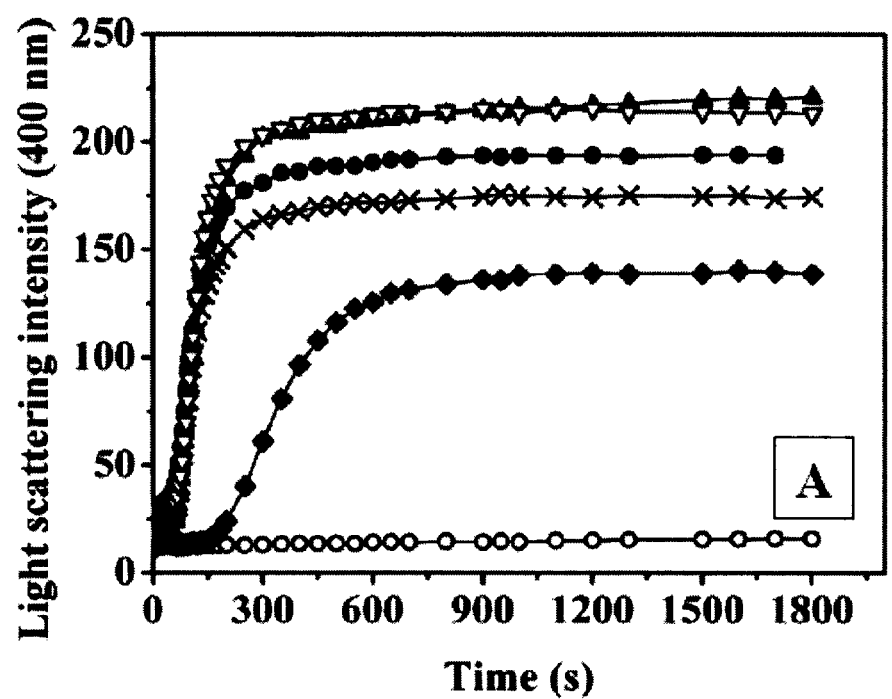

FIG. 3: Additional mechanism of anticancer activity was depolymerization of microtubules. It shows effect of compounds on the assembly of purified tubulin. Light scattering signals for tubulin assembly were monitored for 30 min after initiating the polymerization of tubulin (10 μM) without (▲) (control) or with compound 1 (●), compound 2 (×), compound 3 (▽), and compound 5 (♦). Compound 5 showed maximum potency in this respect.

Figure 4:
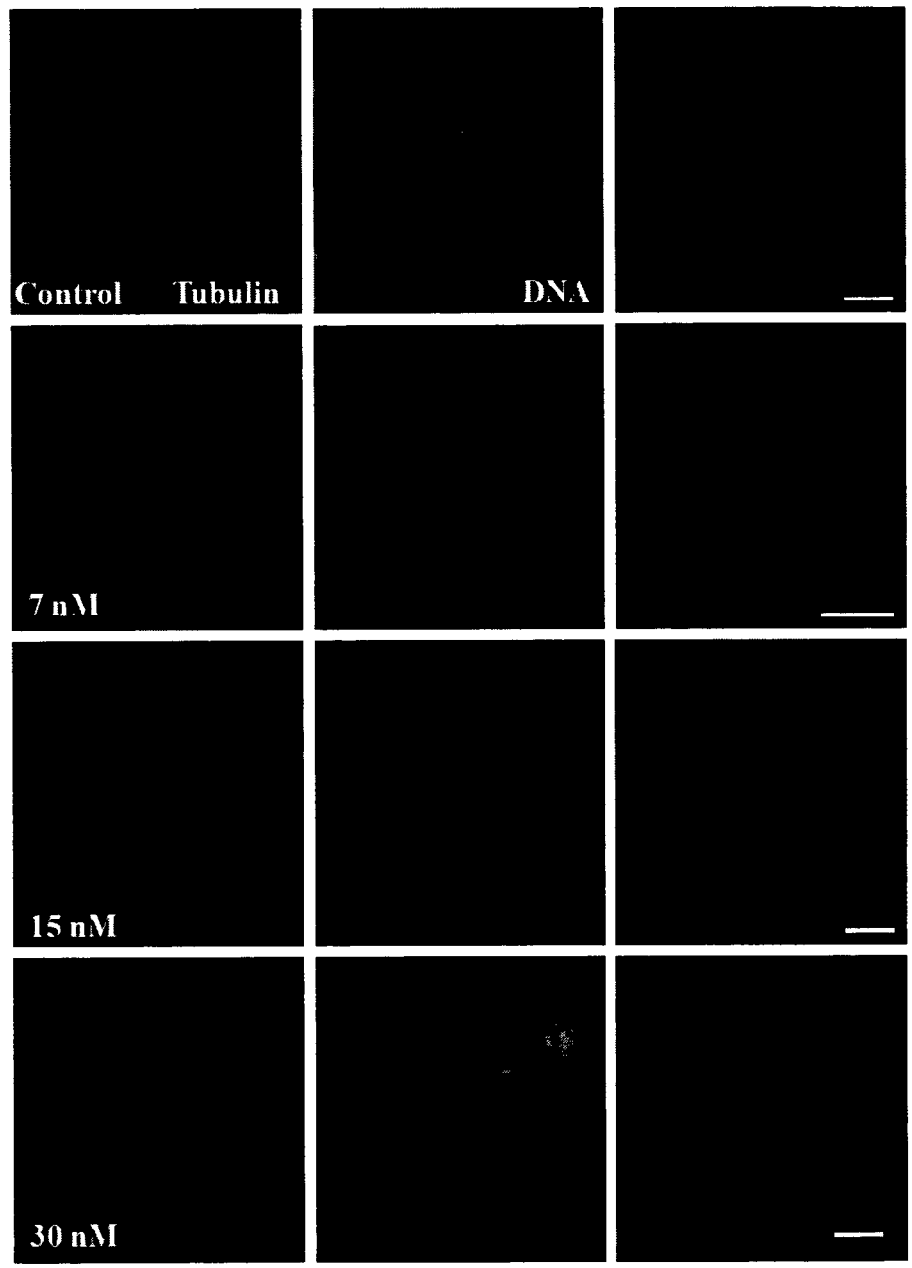

FIG. 4: D5 perturbed microtubule network in HeLa cells: (A) Effects of D5 on the interphase microtubules of HeLa cells are shown. HeLa cells were incubated in the absence or presence of different concentrations (7, 15, 30 nM) of D5 for 24 h. Microtubules (red) and chromosomes (blue) are shown. Scale bar equals 10 μm.

Figure 5:
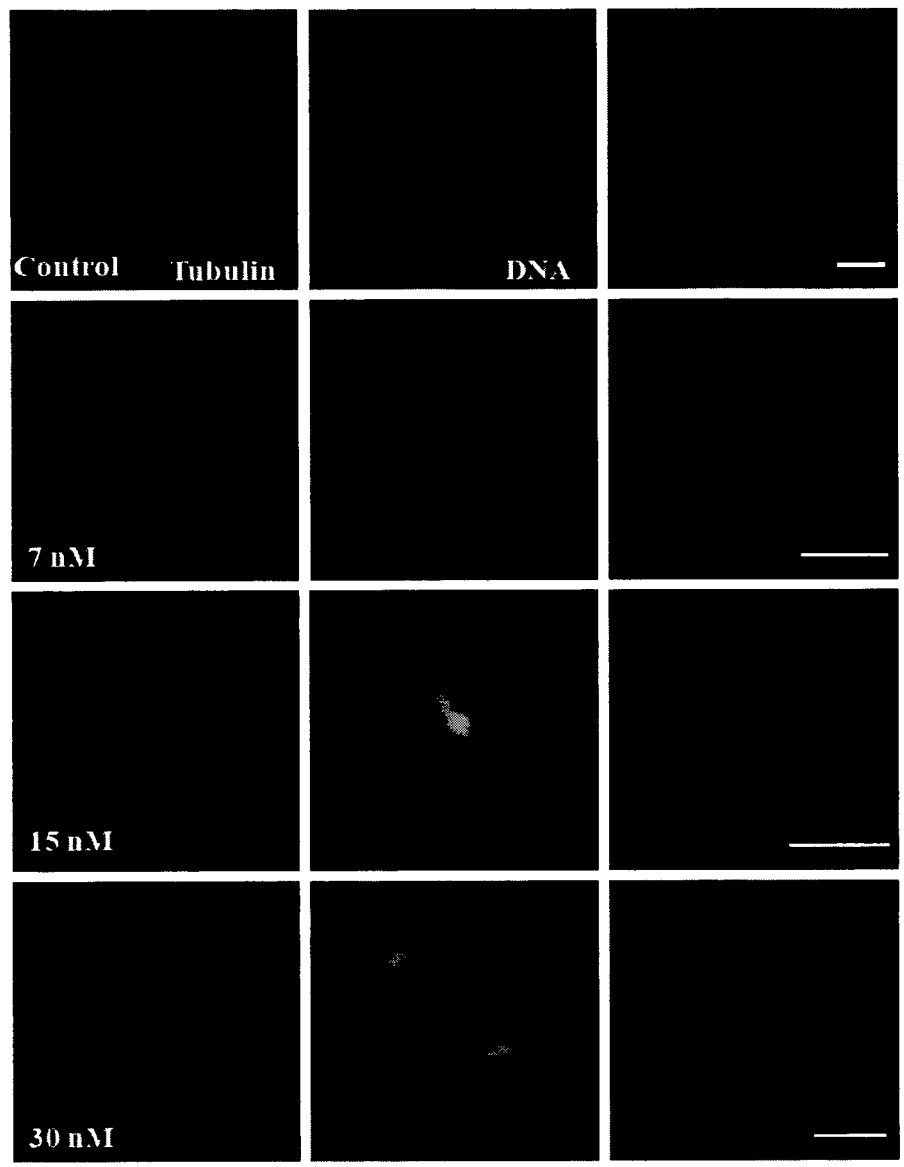

FIG. 5: D5 perturbed microtubule network in HeLa cells: (A) Effects of D5 on the mitotic microtubules of HeLa cells are shown. HeLa cells were incubated in the absence or presence of different concentrations (7, 15, 30 nM) of D5 for 24 h. Microtubules (red) and chromosomes (blue) are shown. Scale bar equals 10 μm.

Figure 6:
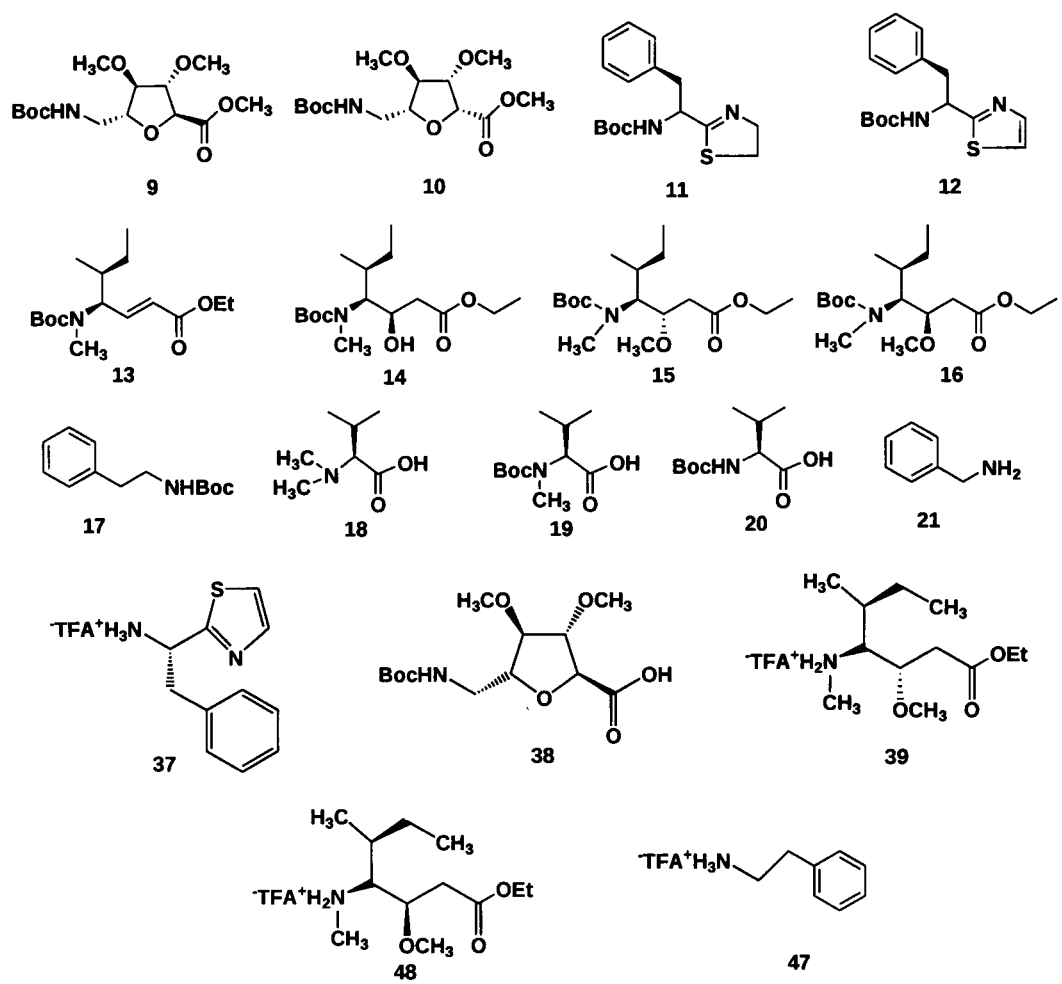

FIG. 6: Monomeric units protected and deprotected form used for the synthesis of anti-cancer peptides 1-8.

Figure 7:
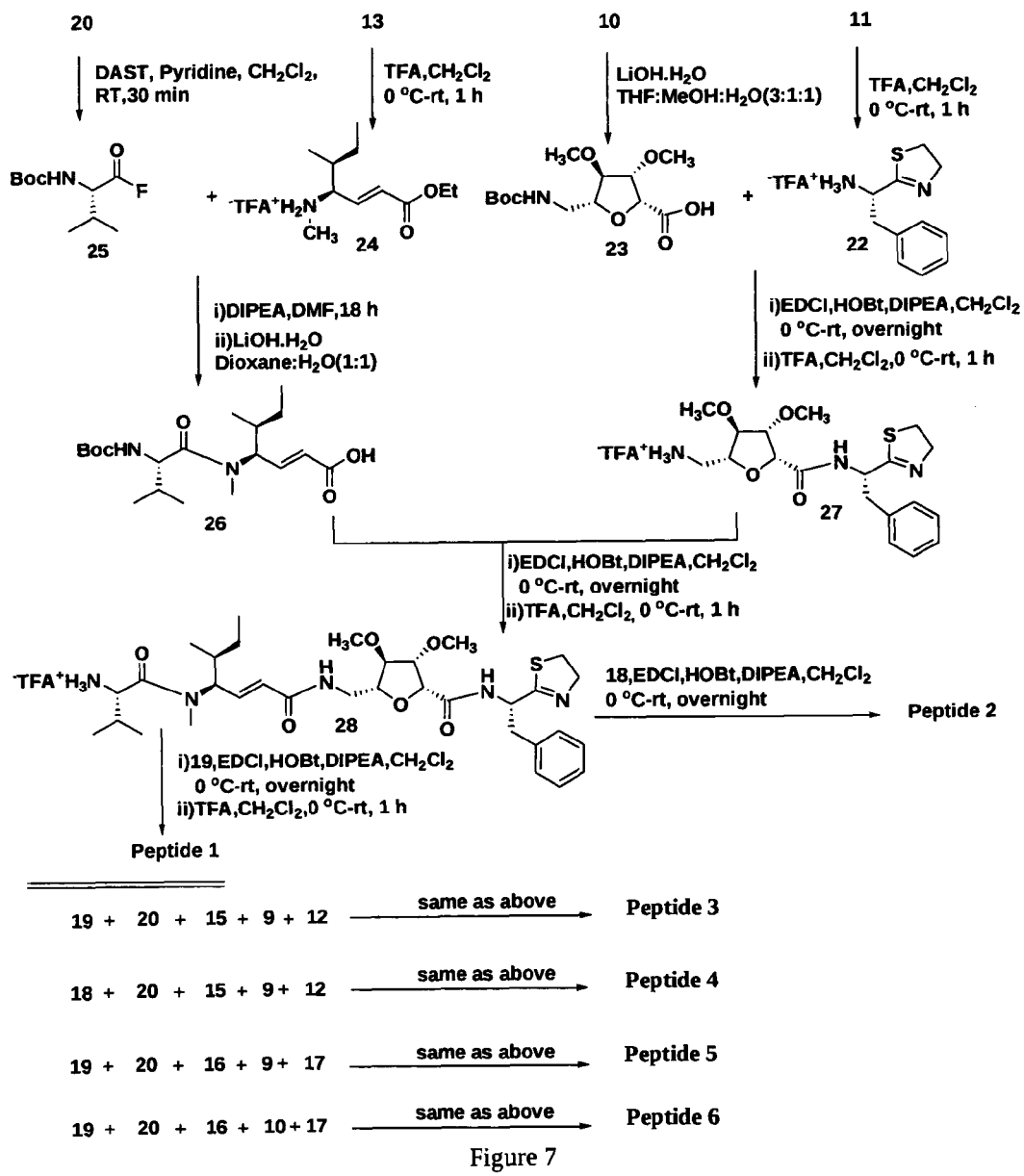

FIG. 7: Scheme for general method of preparation of anti-cancer peptides 1 and 2 in detail and 3 to 6 in concise (Example 1 to 6).

Figure 8:
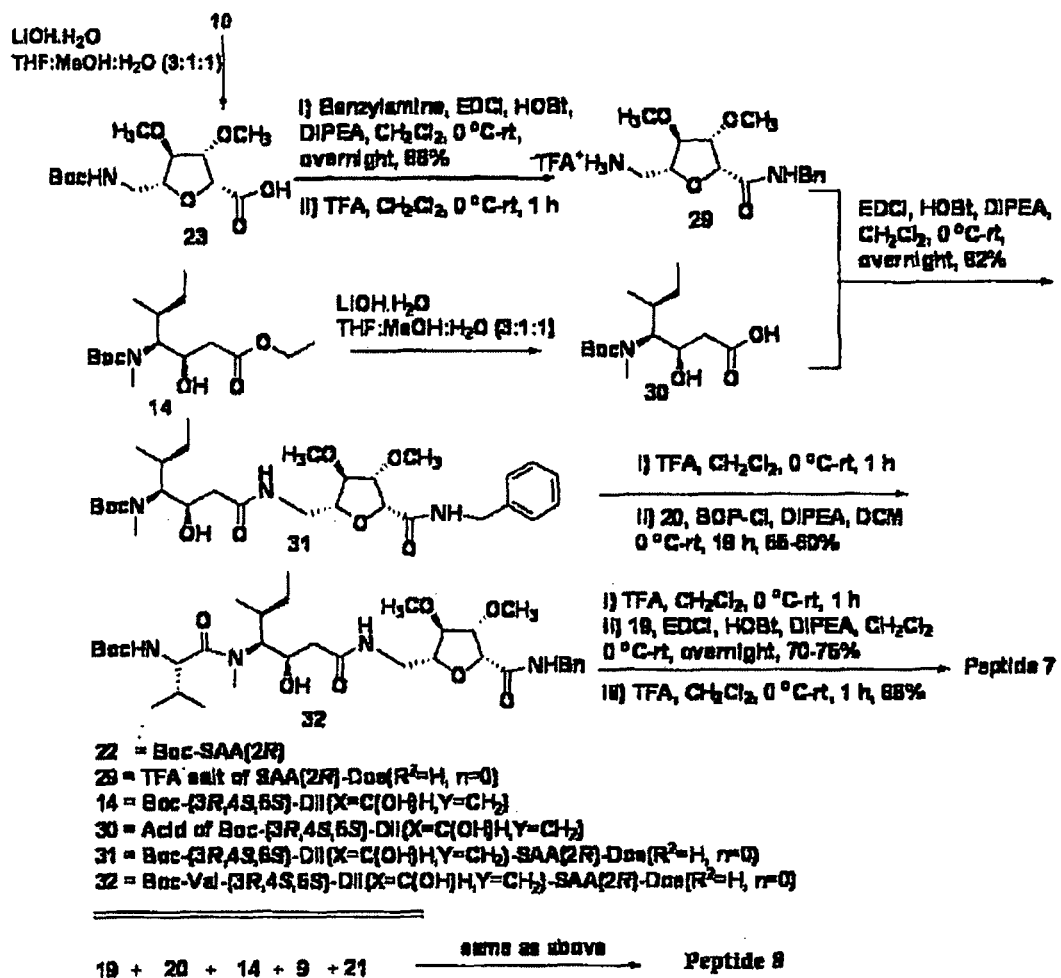

FIG. 8: Scheme for general method of preparation of anti-cancer peptide 7 in detail and 8 in concise (Example 7 & 8).

Figure 9:
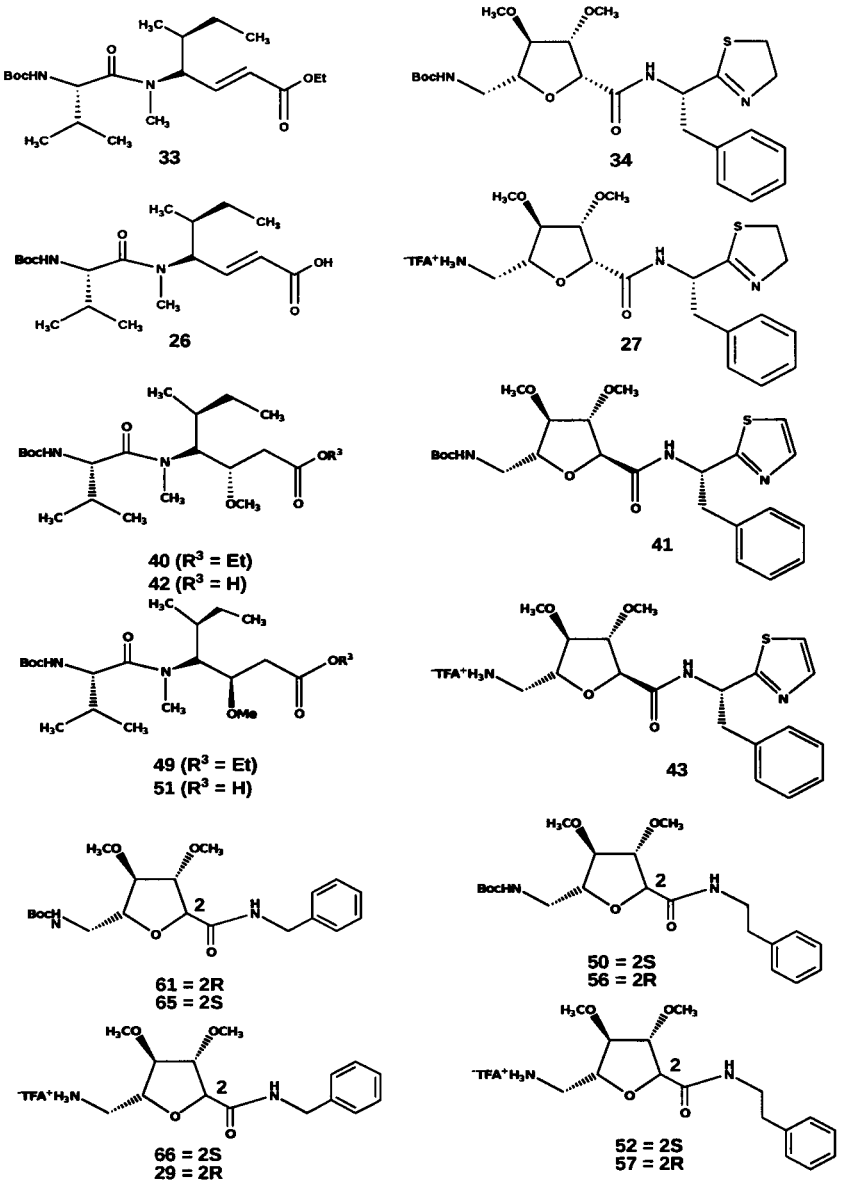

FIG. 9: Intermediate dipeptide compounds in their protected and deprotected forms.

Figure 10:
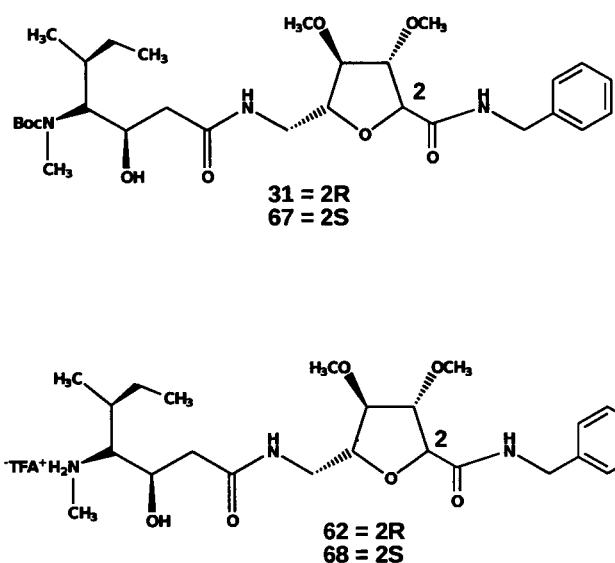

FIG. 10: Intermediate tripeptide compounds in their protected and deprotected forms.

Figure 11:
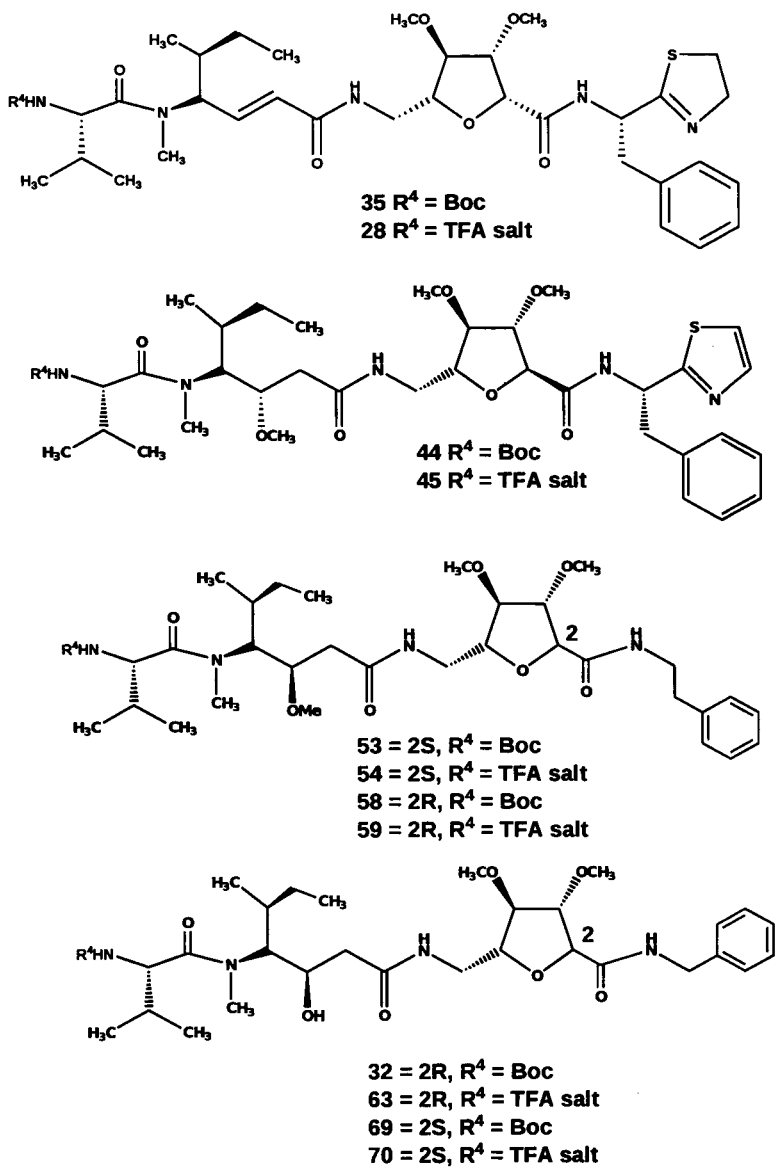

FIG. 11: Intermediate tetrapeptide compounds in their protected and deprotected forms.

Figure 12:
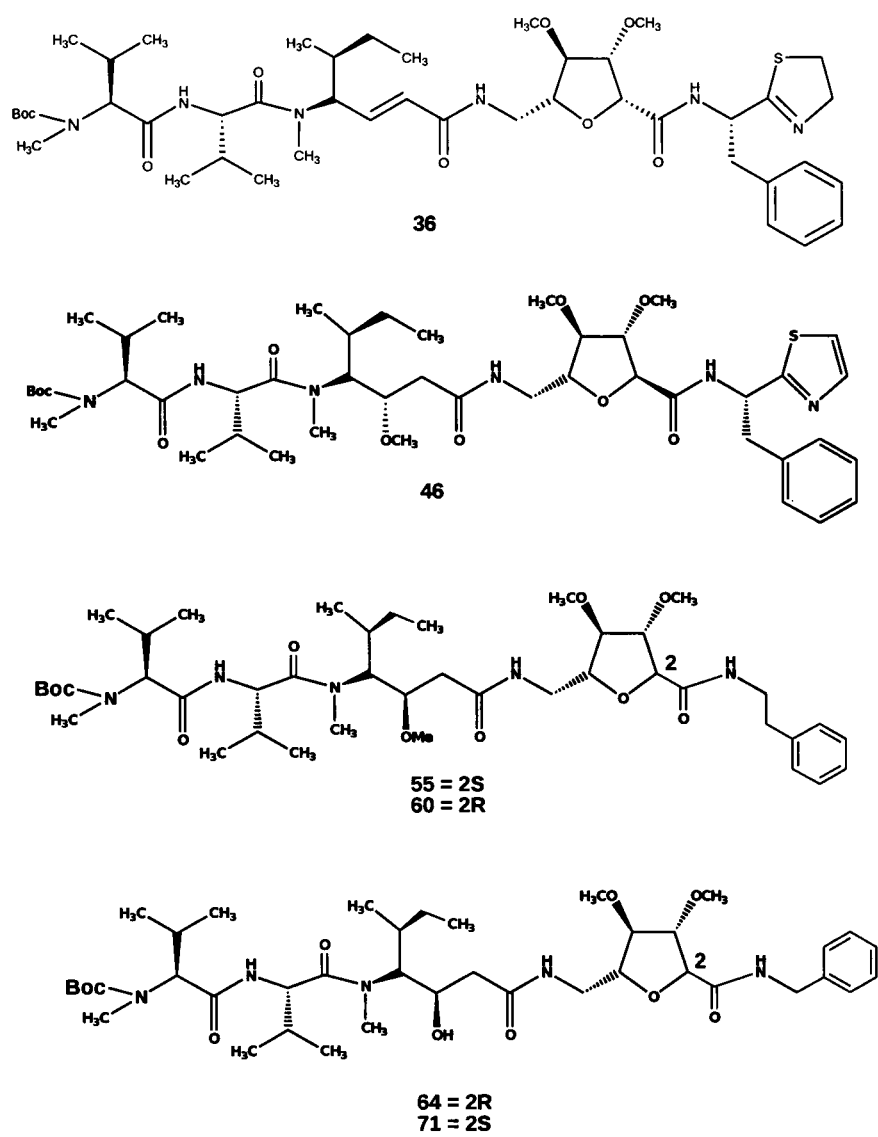

FIG. 12: pentapeptide compounds in their protected forms.

Figure 13:
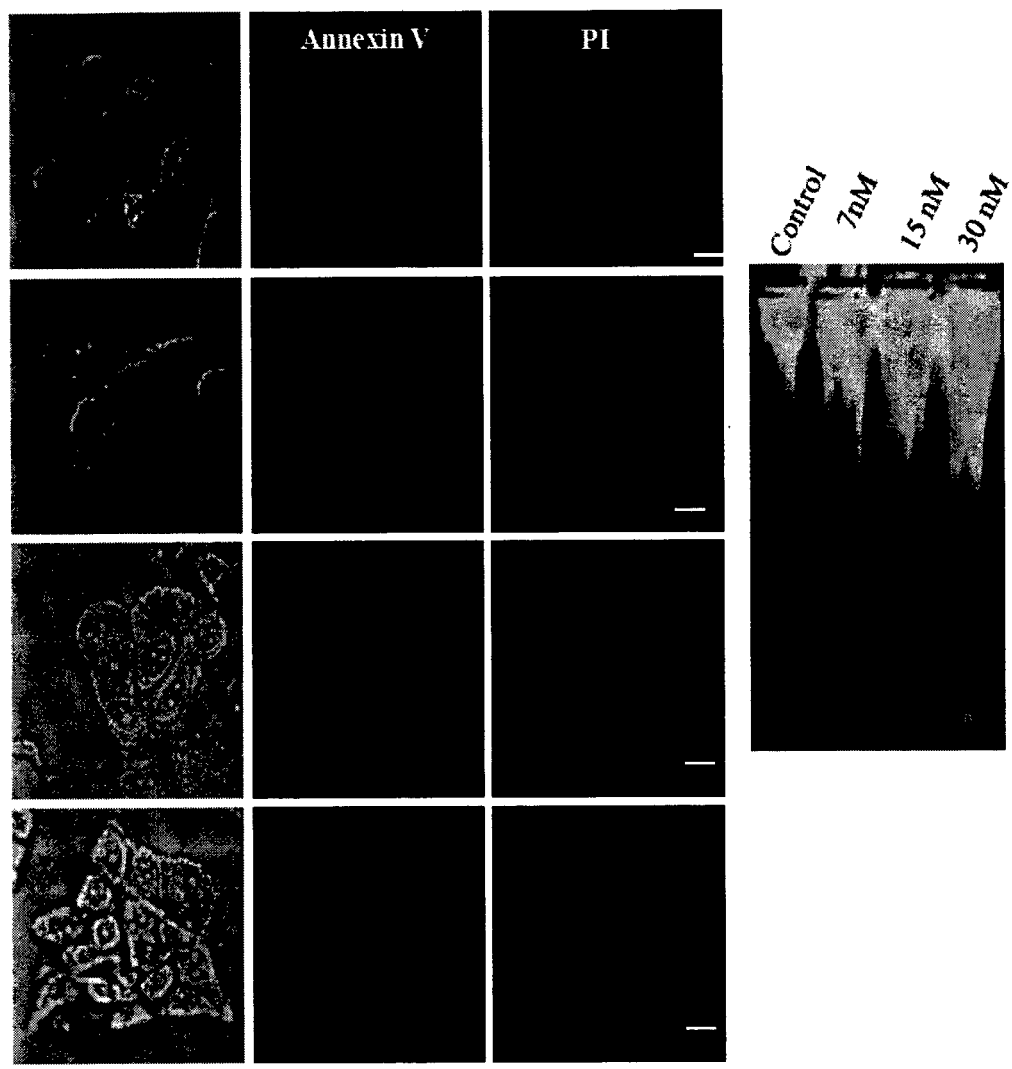

FIG. 13: D5 induced apoptosis in HeLa cells. HeLa cells were treated with different concentrations of D5 (7, 15, 30 nM) for 24 h. The panels display Annexin V and PI staining of the D5 treated cells (B) D5 caused genomic DNA fragmentation in HeLa cells. Cells were incubated with different concentrations of D5 (7, 15, 30 nM) for 40 h and then cells were lysed in buffer and samples were prepared as described in the Material and Methods.

ABBREVIATIONS

Boc: tert-Butyloxycarbonyl
BOP-Cl: Bis(2-oxo-3-oxazolidinyl)phosphonic chloride
DAST: (Diethylamino)sulfur trifluoride
DCM: Dichloromethane
DIPEA: N,N-isopropylethylamine
DMF: N,N-Dimethylformamide
EDCI: 1-Ethyl-3-(3-(dimethylamino)propyl)carbodiimide hydrochloride
EtOAc: Ethyl acetate
HOBt: 1-Hydroxybenzotriazole hydrate
MeOH: Methyl alcohol
TFA: Trifluoroacetic acid
THF: Tetrahydrofuran
HATU: O-(7-Azabenzotriazol-1-yl)-N',N',N',N'-tetramethylyuronium hexafluoro Phosphate

DETAILED DESCRIPTION OF THE INVENTION

The present invention provides novel oligopeptide compounds which have application in cancer treatment, particularly breast carcinoma and cervical carcinoma. The oligopeptides of the present invention have been represented by general formula I:

General formula I

[Chemical structure showing: Dov — Val — Dil — SAA — Doe]

Dov=(S)-Dolavaline, wherein $R^1$ can be H, Me.
Val=(S)-Valine
Dil=Dolaisoleucine, wherein X=C(OH)H, C(OCH$_3$), CH. and Y=CH$_2$, CH.
SAA=Sugar Amino Acid, Wherein SAA can be 2R, 2S.
Doe=(S)-Dolapheine, wherein $R^2$ can be H, 2-(thiazolyl), 2-(4,5-dihydrothiazolyl), and n=0.1.

These anticancer compounds have been prepared by a novel process. The process of preparation of compounds of formula (I) comprises the steps of:

(i) Saponification of ester: LiOH.H$_2$O was added to a solution of compound in THF/MeOH/H$_2$O and the mixture was stirred at room temperature. The mixture was then acidified to pH 2 with 1N HCl. The reaction mixture was extracted with ethyl acetate, washed with water and brine, dried (Na$_2$SO$_4$), filtered and concentrated in vacuum to obtain the acid.

(ii) Deprotection of Boc: Trifluoroacetic acid was added to the compound in dichloromethane, and the mixture was stirred at room temperature. The reaction mixture was then concentrated in vacuum, followed by azeotroping with dichloromethane to obtain the trifluoroacetate salt.

(iii) Peptide Coupling with EDCI, HOBt: 1-hydroxybenzotriazole (HOBt) and 1-ethyl-3-(3-(dimethylamino)-propyl) carbodiimide hydrochloride (EDCI) were sequentially added to a stirring solution of the acid obtained in saponification step (i) in dry dichloromethane or DMF. The previously prepared trifluoroacetate salt dissolved in dichloromethane was added to reaction mixture followed by the addition of DIPEA until reaction mixture was basic. After stirring at room temperature, the reaction mixture was diluted with EtOAc/CH$_2$Cl$_2$, washed with 1N HCl solution, saturated NaHCO$_3$ solution, water and brine, dried (Na$_2$SO$_4$), filtered and concentrated in vacuum. Purification was done by silica gel Chromatography.

(iv) Peptide Coupling with Acid Fluoride: A solution of DAST in dichloromethane was added via a cannula to the acid in dichloromethane and pyridine. The reaction mixture was stirred at room temperature, diluted with CH$_2$Cl$_2$, washed with ice-cold water, dried (Na$_2$SO$_4$), filtered, concentrated and crude material was used in the next step without purification.

A solution of the trifluoroacetate salt of amine in anhydrous DMF was treated with the acid fluoride prepared above and DIPEA and stirred at room temperature, diluted with EtOAc, washed with NaHCO$_3$, brine, dried (Na$_2$SO$_4$), filtered, concentrated under vacuum and purified by silica gel column chromatography.

(v) Peptide Coupling with BOP-Cl: To the acid in dichloromethane was added BOP-Cl, followed by previously prepared trifluoroacetate salt dissolved in dichloromethane was cannulated and was followed by addition of DIPEA until reaction mixture was basic. After completion of reaction, the reaction mixture was diluted with EtOAc, washed with NH$_4$Cl solution, 1N HCl solution, saturated NaHCO$_3$, water and brine, dried (Na$_2$SO$_4$), filtered, concentrated in vacuum and purified by silica gel column chromatography.

The individual steps of preparation of the representative compounds 1 to 8 of general formula I have been explained in the working examples which follow, since the coupling procedures vary from compound to compound.

The following examples are given by way of illustration only and should not be construed so as to limit the scope of this invention.

Example-1

Process of Preparation of Compound 1 (Dov(R$^1$=H)-Val-(4S,5S)-Dil(X,Y=CH)-SAA(2R)-Doe(R$^2$=2-(4,5-dihydrothiazolyl), n=1))

i. As shown in FIG. 7, convergent preparation of compound 1, was started with the compound 11 in dichloromethane, to the compound was added trifluoroacetic acid and the mixture was stirred at room temperature, the reaction mixture was then concentrated in vacuum, followed by azeotroping with dichloromethane to obtain the trifluoroacetate salt 22.

ii. To the compound 10, in THF/MeOH/H$_2$O (3:1:1) was added LiOH.H$_2$O and the mixture was stirred at room temperature, the mixture was then acidified to pH 2 with 1N HCl, the reaction mixture was extracted with ethyl acetate, washed with water and brine, dried (Na$_2$SO$_4$), filtered and concentrated in vacuum to obtain the acid 23.

iii. To a stirring solution of the acid 23 in dry dichloromethane or DMF were sequentially added 1-hydroxybenzotriazole (HOBt) and 1-ethyl-3-(3-(dimethylamino)-propyl)carbodimide hydrochloride (EDCI), the previously prepared trifluoroacetate salt 22 dissolved in dichloromethane was added to reaction mixture followed by the addition of DIPEA until reaction mixture was basic, after stirring at room temperature, the reaction mixture was diluted with EtOAc/CH$_2$Cl$_2$, washed with 1N HCl solution, saturated NaHCO$_3$ solution, water and brine, dried (Na$_2$SO$_4$), filtered and concentrated in vacuum, Purification was done by silica gel Chromatography to provide the dipeptide 34. To dipeptide 34 in dichloromethane, was added trifluoroacetic acid and the mixture was stirred at room temperature, the reaction mixture was then concentrated in vacuum, followed by azeotroping with dichloromethane to obtain the trifluoroacetate salt 27.

iv. To the acid 20 in dichloromethane and pyridine was added via a cannula a solution of DAST in dichloromethane, the reaction mixture was stirred at room temperature, diluted with CH$_2$Cl$_2$, washed with ice-cold water, dried (Na$_2$SO$_4$), filtered, concentrated to provide compound 25.

v. To the compound 13 was added trifluoroacetic acid and the mixture was stirred at room temperature, the reaction mixture was then concentrated in vacuum, followed by azeotroping with dichloromethane to obtain the trifluoroacetate salt 24.

vi. A solution of the trifluoroacetate salt 24 in anhydrous DMF was treated with the acid fluoride 25 prepared above and DIPEA and stirred at room temperature, diluted with EtOAc, washed with NaHCO$_3$, brine, dried (Na$_2$SO$_4$), filtered, concentrated under vacuum and purified by silica gel column chromatography to give dipeptide 33. To dipeptide 33, in Dioxane:H$_2$O (1:1) was added LiOH.H$_2$O and the mixture was stirred at room temperature, the mixture was then acidified to pH 2 with 1N HCl, the reaction mixture was extracted with ethyl acetate, washed with water and brine, dried (Na$_2$SO$_4$), filtered and concentrated in vacuum to obtain the acid 26.

vii. To acid 26, prepared by saponification Process (as used for 10, except the solvent was changed to Dioxane and water) in dry dichloromethane or DMF were sequentially added 1-hydroxybenzotriazole (HOBt) and 1-ethyl-3-(3-(dimethylamino)-propyl)carbodimide hydrochloride (EDCI), the previously prepared trifluoroacetate salt 27 dissolved in dichloromethane was added to reaction mixture followed by the addition of DIPEA until reaction mixture was basic, after stirring at room temperature, the reaction mixture was diluted with EtOAc/CH$_2$Cl$_2$, washed with 1N HCl solution, saturated NaHCO$_3$ solution, water and brine, dried (Na$_2$SO$_4$), filtered and concentrated in vacuum, Purification was done by silica gel Chromatography to provide the tetrapeptide 35. To tetrapeptide 35 compound in dichloromethane, was added trifluoroacetic acid and the mixture was stirred at room temperature, the reaction mixture was then concentrated in vacuum, followed by azeotroping with dichloromethane to obtain the trifluoroacetate salt 28.

viii. To a stirring solution of the acid 19 in dry dichloromethane or DMF were sequentially added 1-hydroxybenzotriazole (HOBt) and 1-ethyl-3-(3-(dimethylamino)-propyl)carbodimide hydrochloride (EDCI), the previously prepared trifluoroacetate salt of tertrapeptide 28 dissolved in dichloromethane was added to reaction mixture followed by the addition of DIPEA until reaction mixture was basic, after stirring at room temperature, the reaction mixture was diluted with EtOAc/CH$_2$Cl$_2$, washed with 1N HCl solution, saturated NaHCO$_3$ solution, water and brine, dried (Na$_2$SO$_4$), filtered and concentrated in vacuum, Purification was done by silica gel Chromatography to provide pentapeptide 36.

ix. Pentapetide compound 36 (40 mg, 0.04 mmol) was dissolved in $CH_2Cl_2$ (4 mL) and cooled to 0° C. followed by the addition of trifluoroacetic acid (1 mL). Reaction mixture was stirred for 1 h and the reaction mixture was poured in a centrifuge tube containing anhydrous diethyl ether (15 mL). Immediately solid came out and it was centrifuged. The solid material was washed with anhydrous diethyl ether (2×15 mL) to get pure TFA-salt 1 (36 mg, 90%) as white solid; IR (neat): $v_{max}$ 3276, 3071, 2927, 1663, 1543, 1461, 1195, 1135, 753 $cm^{-1}$; $^1H$ NMR (400 MHz, $Me_2SO$-$d_6$): δ8.91-8.69 (m, 2H), 7.92 (brs, 1H), 7.14-7.34 (m, 6H), 6.68 (m, 1H), 6.03 (m, 1H), 4.86-4.40 (m, 3H), 4.27 (m, 1H), 3.62-4.02 (m, 4H) 3.48-3.10 (m, 10H), 3.38 (s, 3H), 3.29 (s, 3H), 3.02-2.87 (m, 5H), 2.96 (s, 3H), 2.78-2.68 (m, 2H), 2.43 (s, 3H), 1.93-2.17 (m, 3H), 1.36-1.14 (m, 2H), 1.04-0.69 (m, 18H); $^{13}C$ NMR (75 MHz, $Me_2SO$-$d_6$): δ 171.32, 167.85, 166.08, 152.93, 147.03, 132.01, 129.31, 128.96, 128.17, 127.94, 110.97, 89.31, 86.22, 83.49, 81.59, 50.64, 55.71, 57.25, 56.64, 41.30, 40.75, 33.86, 33.62, 32.02, 30.04, 29.49, 25.71, 18.64, 18.55, 18.29, 17.57, 15.82, 10.52; MS (ESIMS): m/z (%): 777 (100) $[M+NH_4]^+$; HRMS (ESIMS): calculated for $C_{39}H_{66}N_7O_7S$ $[M+NH_4]^+$: 776.4271; found: 776.9342.

Example-2

Process of Preparation of Compound 2 (Dov ($R^1$=Me)-Val-(4S,5S)-Dil(X,Y═CH)-SAA(2R)-Doe ($R^2$=2-(4,5-dihydrothiazolyl), n=1))

Similar steps used for the synthesis of compound 1 (as shown in FIG. 7 & Example 1) was applied for the synthesis of compound 2, with difference in final preparation of pentapeptide wherein the compound 18 was used in place of 19.

To a stirring solution of crude acid 18 (59.3 mg, 0.409 mmol) in dry DMF (2 ML) at 0° C., were sequentially added Hydroxy benzotriazole (55.20 mg, 0.409 mmol) and 1-ethyl-3-(3-(dimethylamino)-propyl)carbodimide hydrochloride (78.40 mg, 0.409 mmol). After 10 min, the previously prepared trifluoroacetate salt of tetrapeptide 28 (100 mg, 0.136 mmol) dissolved in dry DMF (1 ML) was added to reaction mixture followed by the addition of DIPEA (0.07 mL, 0.409 mmol) or until Reaction mixture is basic. After stirring for 12 h at room temperature, the reaction mixture was diluted with EtOAc/DCM, washed with 1N HCl solution, saturated $NaHCO_3$ solution, water, and brine, dried ($Na_2SO_4$), filtered and concentrated in vacuum. Purification by silica gel column chromatography afforded the coupling product ($SiO_2$, 3% to 4% MeOH in $CHCl_3$ eluant) afforded 2 (84.0 mg, 80%). $R_f$=0.3 ($SiO_2$, 5% MeOH in $CHCl_3$); IR (neat): $v_{max}$ 3287, 2925, 2858, 1665, 1541, 1463, 1189, 1082, 969, 754 $cm^{-1}$; $^1H$ NMR (300 MHz, $CDCl_3$): δ 8.12 (d, J=8.3 Hz, 1H), 7.29 (d, J=8.3 Hz, 1H), 7.24-7.10 (m, 5H), 6.72 (dd, J=15.1, 9.0 Hz, 1H), 6.25 (d, J=9.0 Hz, 1H), 6.03 (d, J=15.1 Hz, 1H), 5.10-5.01 (m, 1H), 4.75-4.61 (m, 1H), 4.50-4.39 (m, 2H), 4.19-3.97 (m, 2H), 3.84-3.74 (m, 1H), 3.56-3.48 (m, 1H), 3.36-3.03 (m, 10H), 3.29 (s, 3H), 3.24 (s, 3H), 2.92 (s, 3H), 2.37-2.15 (m, 10H), 2.24 (s, 6H), 1.07-1.27 (m, 2H), 0.99-0.68 (m, 18H); $^{13}C$ NMR (75 MHz, $CDCl_3$): δ 172.82, 170.94, 168.58, 161.07, 147.05, 139.24, 129.16, 128.44, 126.83, 124.43, 123.94, 123.43, 119.04, 84.74, 84.12, 82.08, 58.20, 57.28, 54.18, 42.46, 41.87, 34.84, 33.82, 31.90, 31.41, 30.17, 29.33, 29.14, 27.18, 25.98, 24.86, 22.67, 19.35, 19.20, 18.01, 15.86, 14.10, 11.81; MS (ESIMS): m/z (%): 795 (100) $[M+Na]^+$; HRMS (ESIMS): calcd for $C_{40}H_{20}N_6O_7NaS$ $[M+Na]^+$: 795.4454; found: 795.4415.

Example-3

Process of Preparation of Compound 3 (Dov($R^1$=H)-Val-(3S,4S,5S)-Dil(X═C($OCH_3$)H,Y═$CH_2$)-SAA (2S)-Doe($R^2$=2-(thiazolyl), n=1))

Similar steps used for the synthesis of compound 1 (as shown in FIG. 7 & Example 1) was applied for the synthesis of compound 3, with the difference that compounds 15, 9, 12 were used in place of 13, 10, 11.

Pentapeptide compound 46 (40 mg, 0.04 mmol) was dissolved in $CH_2Cl_2$ (4 mL) and cooled to 0° C. followed by the addition of trifluoroacetic acid (1 mL). Reaction mixture was stirred for 1 h and the reaction mixture was poured in a centrifuge tube containing anhydrous diethyl ether (15 mL). Immediately solid came out and it was centrifuged. The solid material was washed with anhydrous diethyl ether (2×15 mL) to get pure TFA-salt compound 3 (33 mg, 92%) as white solid; IR (neat): $v_{max}$ 3395, 3280, 2969, 2935, 2361, 1669 m 1522, 1465, 1420, 1198, 1102, 752, 719 $cm^{-1}$; $^1H$ NMR (300 MHz, $CDCl_3$): δ 8.71 (s, 1H), 8.44 (d, J=8.6 Hz, 1H), 8.18 (brs, 1H), 7.76 (s, 1H), 7.32-7.12 (m, 6H), 5.35 (m, 1H), 4.66 (m, 1H), 4.33-4.16 (m, 3H), 4.08-3.93 (m, 3H), 3.85-3.19 (m, 12H), 3.21 (s, 3H), 3.13 (s, 3H), 3.01 (s, 3H), 2.42 (s, 3H), 2.32-2.18 (m, 2H), 1.94-1.80 (m, 3H), 1.30-1.10 (m, 2H), 1.01-0.68 (m, 18H); $^{13}C$ NMR (75 MHz, $CDCl_3$): δ 173.56, 171.96, 169.82, 166.39, 164.90, 147.55, 142.22, 129.18, 1228.13, 126.43, 120.03, 87.51, 85.07, 82.03, 79.10, 77.68, 73.11, 65.87, 60.05, 56.83, 56.58, 54.03, 51.90, 34.68, 31,61, 30.64, 29.76, 24.86, 21.79, 19.34, 18.10, 17.75, 15.46, 10.52; MS (ESIMS): m/z (%): 789 (100) $[M+H]^+$; HRMS (ESIMS): calcd for $C_{40}H_{65}N_6O_8S$ $[M+H]^+$: 789.4584; found: 789.4562.

Example-4

Process of Preparation of Compound 4 (Dov ($R^1$=Me)-Val-(3S,4S,5S)-Dil(X═C($OCH_3$)H, Y═$CH_2$)-SAA(2S)-Doe($R^2$=2-(thiazolyl), n=1))

Similar steps used for the synthesis of compound 2 (as shown in FIG. 7 & Example 1) was applied for the synthesis of peptide compound 4, with the difference that compounds 15, 9, 12 were used in place of 13, 10, 11.

To a stirring solution of crude acid 18 (42.0 mg, 0.29 mmol) in dry DMF (2 ML) at 0° C., were sequentially added Hydroxy benzotriazole (39.20 mg, 0.29 mmol) and 1-ethyl-3-(3-(dimethylamino)-propyl)carbodimide hydrochloride (55.65 mg, 0.29 mmol). After 10 min, the previously prepared trifluoroacetate salt of tetrapeptide 45 (75 mg, 0.096 mmol) dissolved in dry DMF (1 ML) was added to reaction mixture followed by the addition of DIPEA (0.05 mL, 0.409 mmol) or until Reaction mixture is basic. After stirring for 12 h at room temperature, the reaction mixture was diluted with EtOAc/DCM, washed with 1N HCl solution, saturated $NaHCO_3$ solution, water, and brine, dried ($Na_2SO_4$), filtered and concentrated in vacuum. Purification by silica gel column chromatography afforded the coupling product. ($SiO_2$, 3% to 4% MeOH in $CHCl_3$ eluant) afforded 4 (62.0 mg, 80%). $R_f$=0.3 ($SiO_2$, 5% MeOH in $CHCl_3$); IR (neat): $v_{max}$ 3289, 3065, 2926, 2362, 1651, 1520, 1461, 1376, 1099, 990, 753, 705 $cm^{-1}$; $^1H$ NMR (300 MHz, $CDCl_3$): δ 7.79 (d, J=3.2 Hz, 1H), 7.44 (d, J=8.1 Hz, 1H), 7.24-7.06 (m, 8H), 5.58 (m, 1H), 4.87 (m, 1H), 4.43 (m, 1H), 4.29-3.87 (m, 4H), 3.69-3.57 (m, 1H), 3.55-3.07 (m, 17H), 3.43 (s, 3H), 3.35 (s, 3H), 3.28 (s, 3H), 3.10 (s, 3H), 2.48-2.17 (m, 8H), 2.24 (s, 6H), 2.14-1.89 (m, 3H), 1.33-1.16 (m, 2H), 1.08-0.7 (m, 18H); $^{13}$C NMR (75 MHz, CDCl$_3$): δ 173.84, 170.89, 170.56, 170.04, 160.96, 142.53, 136.24, 129.43, 128.44, 126.89, 119.07, 87.29, 85.67, 82.94, 82.69, 78.33, 60.85, 58.30, 57.53, 57.34, 56.83, 53.96, 51.56, 41.48, 40.89, 39.48, 32.49, 31.82, 31.43, 31.21, 29.68, 27.88, 25.51, 19.91, 19.01, 17.96, 17.45, 15.87, 10.73; MS (ESIMS): m/z (%): 803 (100) [M+H]$^+$; HRMS (ESIMS): calcd for C$_{41}$H$_{67}$N$_6$O$_8$S [M+H]$^+$: 803.4741; found: 803.4731.

Example-5

Process of Preparation of Compound 5 (Dov(R$^1$=H)-Val-(3R,4S,5S)-Dil(X=C(OCH$_3$)H,Y=CH$_2$)-SAA (2S)-Doe(R$^2$=H, n=1))

Similar steps used for the synthesis of compound 1 (as shown in FIG. 7 & Example 1) was applied for the synthesis of peptide compound 5, with difference is compounds 16, 9, 17 were used in place of 13, 10, 11.

Pentapeptide compound 55 (40 mg, 0.05 mmol) was dissolved in CH$_2$Cl$_2$ (4 mL) and cooled to 0° C. followed by the addition of trifluoroacetic acid (1 mL). Reaction mixture was stirred for 1 h and the reaction mixture was poured in a centrifuge tube containing anhydrous diethyl ether (15 mL). Immediately solid came out and it was centrifuged. The solid material was washed with anhydrous diethyl ether (2×15 mL) to get pure TFA-salt 5 (30 mg, 85%) as white solid; IR (neat): ν$_{max}$ 3291, 3067, 2968, 2936, 1654, 1541, 1462, 1421, 1197, 1100, 838, 752, 719 cm$^{-1}$; $^1$H NMR (300 MHz, CDCl$_3$): δ 8.90-8.68 (m, 2H), 8.05 (m, 2H), 7.87 (m, 2H), 7.36-7.12 (m, 5H), 4.69-4.16 (m, 3H), 4.03 (m, 1H), 3.96-3.82 (m, 2H), 3.75-3.60 (m, 2H), 3.47-3.13 (m, 13H), 3.32 (s, 3H), 3.21 (s, 3H), 2.98 (s, 3H), 2.80-2.63 (m, 3H), 2.46 (s, 3H), 2.36-2.18 (m, 2H), 2.15-1.94 (m, 2H), 1.22 (m, 1H), 1.10 (m, 1H), 1.03-0.69 (m, 18H); $^{13}$C NMR (75 MHz, CDCl$_3$): δ 174.59, 170.15, 166.46, 158.64, 139.85, 129.01, 128.71, 126.52, 88.11, 85.53, 82.74, 82.42, 78.52, 66.11, 65.41, 57.26, 57.08, 55.03, 38.55, 35.47, 32.48, 30.49, 29.97, 29.69, 25.81, 20.42, 19.16, 18.92, 18.73, 18.07, 16.12, 15.70, 10.95; MS (ESIMS): m/z (%): 706 (100) [M+H]$^+$; HRMS (ESIMS): calcd for C$_{37}$H$_{64}$N$_5$O$_8$ [M+H]$^+$: 706.4754; found: 706.4754.

Example-6

Process of Preparation of Compound 6 (Dov(R$^1$=H)-Val-(3R,4S,5S)-Dil(X=C(OCH$_3$)H,Y=CH$_2$)-SAA (2R)-Doe(R$^2$=H, n=1))

Similar steps used for the synthesis of compound 1 (as shown in FIG. 7 & Example 1) was applied for the synthesis of peptide compound 6, with difference is compounds 16, 10, 17 were used in place of 13, 10, 11.

Pentapeptide compound 60 (40 mg, 0.05 mmol) was dissolved in CH$_2$Cl$_2$ (4 mL) and cooled to 0° C. followed by the addition of trifluoroacetic acid (1 mL). Reaction mixture was stirred for 1 h and the reaction mixture was poured in a centrifuge tube containing anhydrous diethyl ether (15 mL). Immediately solid came out and it was centrifuged. The solid material was washed with anhydrous diethyl ether (2×15 mL) to get pure TFA-salt 6 (32 mg, 91%) as white solid; IR (neat): ν$_{max}$ 3279, 3070, 2968, 2934, 2361, 1651, 1545, 1462, 1422, 1197, 1129, 1093, 752 cm$^{-1}$; $^1$H NMR (400 MHz, Me$_2$SO-d$_6$): δ 8.79 (d, J=8.05 Hz, 1H), 8.69 (brs, 1H), 8.14 (m, 1H), 7.84 (m, 1H), 7.34-7.15 (m, 5H), 4.58 (m, 1H), 4.25 (d, J=3.5 Hz, 1H) 3.90 (d, J=3.5 Hz, 1H), 3.87-3.81 (m, 2H), 3.74-3.62 (m, 2H), 3.45-3.18 (m, 13H), 3.30 (s, 3H), 3.25 (s, 3H), 3.21 (s, 3H), 2.96 (s, 3H), 2.82-2.17 (m, 6H), 2.46 (s, 3H), 2.13-1.92 (m, 3H), 1.35-1.21 (m, 2H), 0.99-0.70 (m, 18H); $^{13}$C NMR (75 MHz, Me$_2$SO-d$_6$): δ 172.01, 171.89, 167.89, 166.01, 139.39, 128.59, 128.55, 126.12, 83.50, 83.62, 83.81, 82.04, 81.73, 78.10, 77.30, 65.61, 57.47, 57.28, 54.86, 54.59, 54.61, 35.16, 30.06, 29.55, 29.49, 29.07, 25.37, 22.12, 18.69, 18.46, 18.26, 17.62, 15.13, 10.15; MS (ESIMS): m/z (%): 706 (100) [M+H]$^+$; HRMS (ESIMS): calcd for C$_{37}$H$_{64}$N$_5$O$_8$ [M+H]$^+$: 706.4754; found: 706.4778.

Example-7

Process of Preparation of Compound 7 (Dov(R$^1$=H)-Val-(3R,4S,5S)-Dil(X=C(OH)H,Y=CH$_2$)-SAA (2R)-Doe(R$^2$=H, n=0))

i. As shown in FIG. 8, Preparation of compound 7, was started with a stirring solution of the acid 23 in dry dichloromethane or DMF were sequentially added 1-hydroxybenzotriazole (HOBt) and 1-ethyl-3-(3-(dimethylamino)-propyl)carbodimide hydrochloride (EDCI), the 21 dissolved in dichloromethane was added to reaction mixture followed by the addition of DIPEA until reaction mixture was basic, after stirring at room temperature, the reaction mixture was diluted with EtOAc/CH$_2$Cl$_2$, washed with 1N HCl solution, saturated NaHCO$_3$ solution, water and brine, dried (Na$_2$SO$_4$), filtered and concentrated in vacuum, Purification was done by silica gel Chromatography to provide the dipeptide 65. To the dipeptide 65 in dichloromethane, was added trifluoroacetic acid and the mixture was stirred for room temperature, the reaction mixture was then concentrated in vacuum, followed by azeotroping with dichloromethane to obtain the trifluoroacetate salt 29.

ii. To the compound 14, in THF/MeOH/H$_2$O (3:1:1) was added LiOH.H$_2$O and the mixture was stirred at room temperature, the mixture was then acidified to pH 2 with 1N HCl, the reaction mixture was extracted with ethyl acetate, washed with water and brine, dried (Na$_2$SO$_4$), filtered and concentrated in vacuum to obtain the acid 30.

iii. To the acid 30 in dry dichloromethane or DMF were sequentially added 1-hydroxybenzotriazole (HOBt) and 1-ethyl-3-(3-(dimethylamino)-propyl)carbodimide hydrochloride (EDCI), the previously prepared trifluoroacetate salt 29 dissolved in dichloromethane was added to reaction mixture followed by the addition of DIPEA until reaction mixture was basic, after stirring at room temperature, the reaction mixture was diluted with EtOAc/CH$_2$Cl$_2$, washed with 1N HCl solution, saturated NaHCO$_3$ solution, water and brine, dried (Na$_2$SO$_4$), filtered and concentrated in vacuum, Purification was done by silica gel Chromatography to provide the tripeptide 31.

iv. To compound 31 in dichloromethane, was added trifluoroacetic acid and the mixture was stirred for room temperature, the reaction mixture was then concentrated in vacuum, followed by azeotroping with dichloromethane to provide 62.

v. To the acid 20 in dichloromethane was added BOP-Cl, followed by previously prepared trifluoroacetate salt 62 dissolved in dichloromethane was cannulated and was followed by addition of DIPEA until reaction mixture was basic, after completion of reaction, the reaction mixture was diluted with EtOAc, washed with NH$_4$Cl solution, 1N HCl solution, saturated NaHCO$_3$, water and brine, dried (Na$_2$SO$_4$), filtered, concentrated in vacuum and purified by silica gel column chromatography to provide tetrapeptide 32.

vi. To compound 32 in dichloromethane, was added trifluoroacetic acid and the mixture was stirred for room temperature, the reaction mixture was then concentrated in vacuum, followed by azeotroping with dichloromethane to obtain the trifluoroacetate salt 63.

vii. To a stirring solution of the acid 19 in dry dichloromethane or DMF were sequentially added 1-hydroxybenzotriazole (HOBt) and 1-ethyl-3-(3-(dimethylamino)-propyl)carbodimide hydrochloride (EDCI), the previously prepared trifluoroacetate salt of tertrapeptide dissolved in dichloromethane was added to reaction mixture followed by the addition of DIPEA until reaction mixture was basic, after stirring at room temperature, the reaction mixture was diluted with EtOAc/CH$_2$Cl$_2$, washed with 1N HCl solution, saturated NaHCO$_3$ solution, water and brine, dried (Na$_2$SO$_4$), filtered and concentrated in vacuum, Purification was done by silica gel Chromatography to provide pentapetide 64.

viii. Pentapeptide compound 64 (40 mg, 0.05 mmol) was dissolved in CH$_2$Cl$_2$ (4 mL) and cooled to 0° C. followed by the addition of trifluoroacetic acid (1 mL). Reaction mixture was stirred for 1 h and the reaction mixture was poured in a centrifuge tube containing anhydrous diethyl ether (15 mL). Immediately solid came out and it was centrifuged. The solid material was washed with anhydrous diethyl ether (2×15 mL) to get pure TFA-salt 7 (33 mg, 95%) as white solid. IR (neat): $v_{max}$ 3279, 3069, 2968, 2934, 2361, 1653, 1546, 1462, 1423, 1196, 1130, 1090, 751, 721 cm$^{-1}$; δ 8.84-8.69 (m, 2H), 8.80 (m, 1H), 8.27 (m, 1H), 8.15 (m, 1H), 7.45-7.18 (m, 5H), 4.95 (m, 1H), 4.58 (m, 1H) 4.48-4.23 (m, 3H), 4.01-3.25 (m, 10H), 3.34 (s, 3H), 3.30 (s, 3H), 2.99-2.89 (m, 9H), 2.95 (s, 3H), 2.45 (s, 3H), 2.25-1.96 (m, 4H), 1.85-1.72 (m, 1H), 1.48-1.19 (m, 2H), 1.08-0.67 (m, 18H); $^{13}$C NMR (125 MHz, Me$_2$SO-d$_6$): δ 175.90, 170.98, 167.83, 165.90, 139.34, 126.72, 126.43, 83.93, 83.75, 83.38, 81.66, 67.64, 65.51, 57.23, 56.49, 54.21, 41.49, 40.97, 40.45, 33.58, 33.64, 31.97, 29.88, 29.39, 29.34, 25.13, 18.86, 17.65, 18.09, 18.30, 16.16, 11.22; MS (ESIMS): m/z (%): 678 (100) [M+H]$^+$; HRMS (ESIMS): calcd for C$_{35}$H$_{60}$N$_5$O$_8$ [M+H]$^+$: 678.4441; found: 678.4465.

Example-8

Process of Preparation of Compound 8 (Dov(R$^1$=H)-Val-(3R,4S,5S)-Dil(X=C(OH)H,Y=CH$_2$)-SAA (2S)-Doe(R$^2$=H, n=0))

Similar steps used for the synthesis of compound 7 (as shown in FIG. 8 & Example 7) was applied for the synthesis of peptide compound 8, only difference is compound 10 was replaced with compound 9.

Pentapeptide compound 64 (40 mg, 0.05 mmol) was dissolved in CH$_2$Cl$_2$ (4 mL) and cooled to 0° C. followed by the addition of trifluoroacetic acid (1 mL). Reaction mixture was stirred for 1 h and the reaction mixture was poured in a centrifuge tube containing anhydrous diethyl ether (15 mL). Immediately solid came out and it was centrifuged. The solid material was washed with anhydrous diethyl ether (2×15 mL) to get pure TFA-salt 8 (32 mg, 92%) as white solid; IR (neat): $v_{max}$ 3292, 3068, 2934, 1661, 1541, 1462, 1423, 1195, 1126, 834, 752, 722, 665 cm$^{-1}$; δ 8.86-8.67 (m, 2H), 8.82 (d, J=8.4 Hz, 1H), 8.44 (m, 1H), 8.02 (m, 1H), 7.36-7.16 (m, 5H), 4.89 (m, 1H), 4.57 (t, J=8.4 Hz, 1H), 4.40 (m, 1H), 4.35 (d, J=6.4 Hz, 1H), 4.19 (d, J=5.6 Hz, 1H), 4.16-4.07 (m, 2H), 3.97 (m, 1H), 3.72-3.62 (m, 2H), 3.49-3.13 (m, 9H), 3.30 (s, 3H), 3.20 (s, 3H), 2.95 (s, 3H), 2.45 (s, 3H), 2.15 (m, 1H), 2.11-1.93 (m, 2H), 1.89-1.71 (m, 1H), 1.46-1.29 (m, 2H), 1.03-0.67 (m, 18H); $^{13}$C NMR (75 MHz, Me$_2$SO-d$_6$): δ 171.57, 170.92, 169.76, 165.84, 139.35, 127.93, 126.73, 126.39, 87.45, 84.72, 82.38, 67.55, 65.45, 56.58, 56.33, 56.10, 54.21, 41.55, 41.36, 33.51, 31.92, 31.81, 31.39, 29.84, 29.34, 25.09, 18.81, 18.27, 18.07, 17.59, 16.13, 11.16; MS (ESIMS): m/z (%): 678 (100) [M+H]$^+$; HRMS (ESIMS): calcd for C$_{35}$H$_{60}$N$_5$O$_8$ [M+H]$^+$: 678.4441; found: 678.4465.

Example 9

Biological Evaluation

Compounds 1 to 8 were evaluated for their in vitro anticancer activity. Their IC$_{50}$ values against human cervical cancer cell line (HeLa) are shown in Table 1. Similarly, compound 5 also inhibited proliferation of MCF-7 (breast cancer) and MDA-MB-231 (highly metastatic breast cancer) cells. Compound 5 showed maximum potency, with IC$_{50}$ of 6.8 nM in HeLa cells (Table 1).

TABLE 1

IC$_{50}$ values against human cervical cancer cell line (HeLa) of compounds 1-8.

| Compound | IC$_{50}$ against HeLa cells |
|---|---|
| 1 | 8.7 nM |
| 2 | 8.8 nM |
| 3 | 9.9 nM |
| 4 | 16 nM |
| 5 | 6.8 nM |
| 6 | 15 nM |
| 7 | 16 nM |
| 8 | 12 nM |

Determination of IC$_{50}$ in cancer cell lines: Highly metastatic human breast cancer (MDA-MB 231), human breast cancer (MCF-7) and cervical cancer (HeLa) cells were grown in 96-well tissue culture plates at 37° C. for 24 h. Then the medium was replaced with fresh medium containing vehicle (0.1% DMSO) or different concentrations of compounds (1-40 nM) and the cells were grown for an additional 24 h. Both attached and floating cells were harvested and counted after staining with trypan blue (Rathinasamy et al, *BMC Cancer* 2010; 10:213). Percentage inhibition of cell proliferation was plotted against compound concentration using Origin Pro 7.5 software (Table 2).

TABLE 2

IC$_{50}$ values of compound 5 against different cancer cell lines

| Cell line | IC$_{50}$ values for compound 5 |
|---|---|
| HeLa cells | 6.8 ± 0.2 nM |
| MDA-MB-231 cells | 13 ± 5 nM |
| MCF-7 cells | 15 ± 7 nM |

Apoptosis detection by DNA fragmentation assay: HeLa cells were incubated without (control) and with different concentrations of compound 5. After 40 h of incubation, cells were trypsinized and collected by centrifugation. After washing pellet twice in PBS, the cells were lysed in buffer (50 mM Tris pH 8.0, 10 mM EDTA, 0.5% sarcosine, and 0.5 mg/mL proteinase K), and incubated at 50° C. for 1 h in the heating block. RNase A (1 mg/mL) was added and incubation was further extended for 1 h. The samples were allowed to come to 25° C. Gel electrophoresis was done using 2% agarose and the fragmented genomic DNA visualized after staining with ethidium bromide using UV gel documentation system (FIG. 2) (Rathinasamy et al, *FEBS J* 2006; 273:4114). HeLa cells were incubated with different concentrations of compound 5 (7, 15 and 30 nM) for 24 h. Cells were stained with annexin V and propidium iodide. The number of cells undergoing apoptosis was estimated by counting the annexin V and propidium iodide positive cells (FIG. 13). D5 caused genomic DNA fragmentation in HeLa cells.

Microtubule polymerization assay: Goat brain tubulin (10 µM) was incubated without or with different compounds 1, 2, 3 and compound 5 (5 µM) in microtubule assembly buffer (1 M monosodium glutamate, 3 mM $MgCl_2$, 1 mM EGTA and 25 mM PIPES pH 6.8) on ice for 20 minutes. Then, GTP (1 mM) was added to the reaction mixture. The assembly of tubulin was monitored at 37° C. using a spectrofluorometer for 30 min. Similar experiment was done with compound 5 (1, 5, 7 and 10 µM). MAPs-rich tubulin (1 mg/mL) was incubated without or with different concentrations of compound 5 (1, 3, 5 and 10 µM) in PEM buffer (25 mM pipes pH 6.8 containing 3 mM $MgCl_2$ and 1 mM EGTA) for 15 min on ice and then, 1 mM GTP was added to the reaction mixture. The effect of D1, D2, D3 and D5 on the assembly kinetics was monitored as described above for purified tubulin (FIG. 3) (Gupta and Panda, *Biochemistry* 2002; 41:13029) to study depolymerization of microtubules which is a mechanism of anticancer activity.

Effect of Compound 5 on interphase and mitotic microtubules of HeLa cells: HeLa cells were seeded at a density of $0.6 \times 10^5$ cells/mL and were grown as monolayer on glass cover slips. Compounds diluted in Dimethyl sulfoxide (DMSO) (0.1% final concentration) were added to the culture medium 24 h after seeding. Then, the medium was replaced with fresh medium containing vehicle (0.1% DMSO) or different concentrations (7, 15, 30 nM) of compound 5 and the incubation continued for further 24 h. The cells were then fixed with 3.7% formaldehyde at 37° C. for 30 min and immunostained using tubulin antibody (FIGS. 4 and 5) (Mohan R and Panda D, *Cancer Res.* 2008, 68: 6181). The DNA was stained using Hoechst 33258 dye. The images were visualized by TE Eclipse 2000U fluorescence microscope (Nikon, Tokyo, Japan) and analyzed with Image-Pro Plus software.

ADVANTAGES OF THE INVENTION

The main advantage of this invention is to provide novel approach for preparing anticancer peptides.

The anticancer peptides can be prepared in moderate to good yields, which allows for large scale production of these compounds.

Property of good water solubility of these peptides allows easy and appropriate dose regimen.

In view of their observed anti-cancer properties, the possibility exists that these synthetic peptides can become part of the anti-cancer therapy evidently shown by substantial levels of increased apopotosis, depolymerization of mitotic microtubules and inhibition of tubulin polymerization.

We claim:

1. A compound consisting of Formula I, or a pharmaceutically acceptable salt thereof:

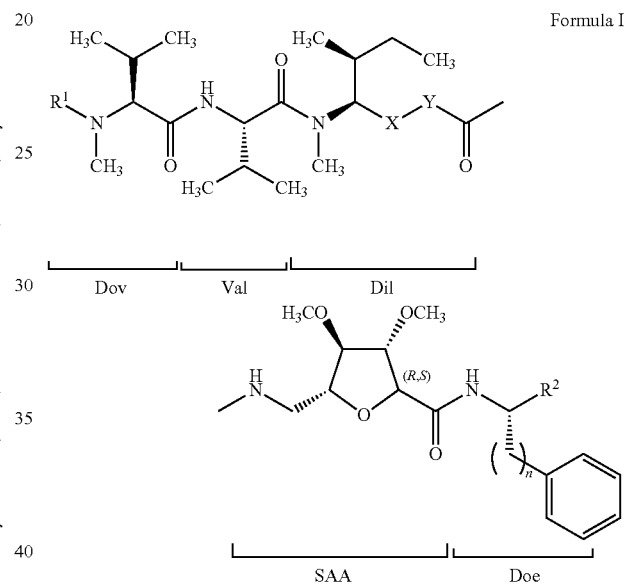

Formula I wherein:
Dov =(S)-Dolavaline, wherein $R^1$ is H or Me
Val =(S)-Valine
Dil =Dolaisoleucine, wherein X=C(OH)H, C($OCH_3$), or CH, and Y=$CH_2$, or CH
SAA =Sugar Amino Acid as depicted above, wherein SAA is 2R or 2S
Doe =(S)-Dolapheine, wherein $R^2$ is H, 2-(thiazolyl), or 2-(4,5-dihydrothiazolyl), and n=0 or 0.1.

2. The compound of claim 1, selected from the group consisting of:

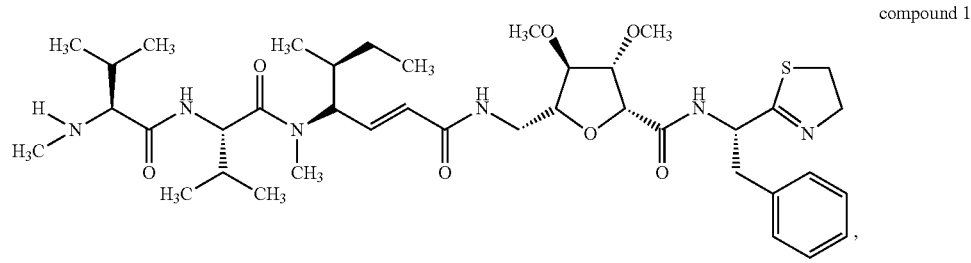

compound 1

-continued
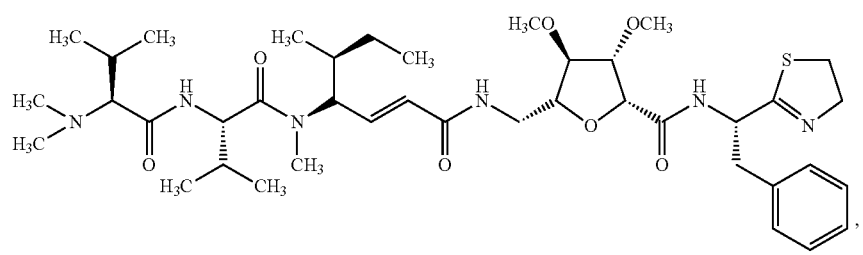
compound 2
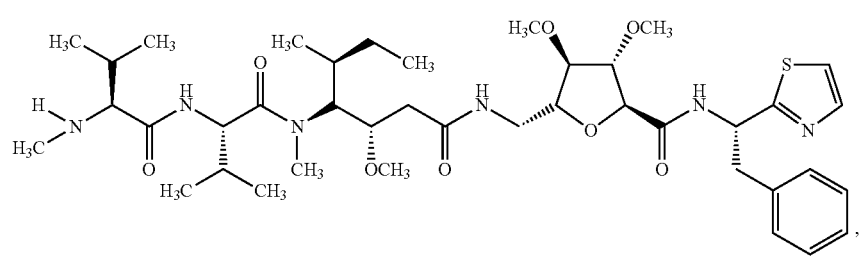
compound 3
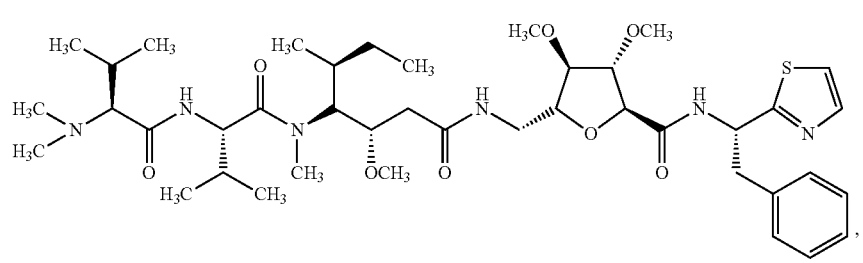
compound 4
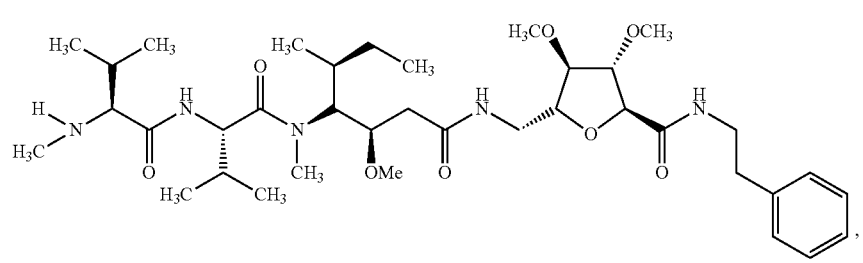
compound 5
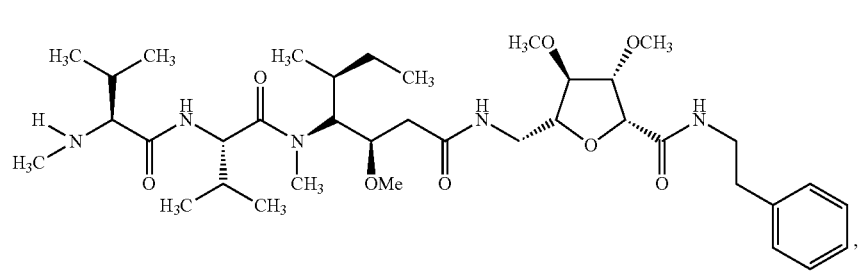
compound 6
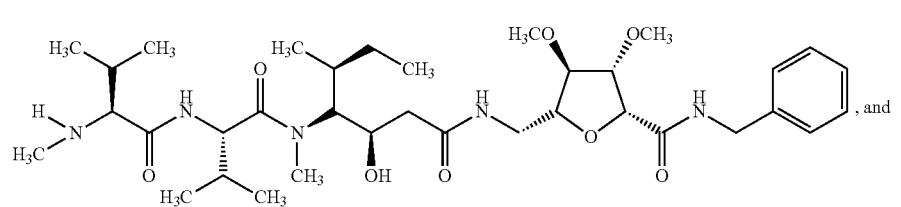
compound 7, and -continued

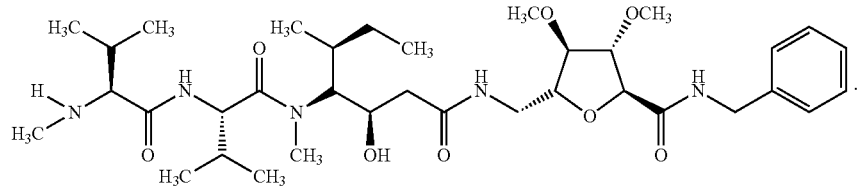

compound 8

3. The compound of claim 1, wherein the pharmaceutically acceptable salt is selected from an acid addition salt formed from a non-toxic organic or inorganic acid.

4. The compound of claim 3, wherein the acid addition salt is derived from an inorganic acid selected from the group consisting of hydrochloric acid, hydrobromic acid, hydroiodic acid, sulfuric acid, phosphoric acid and nitric acid.

5. The compound claim 3, wherein the acid addition salt is derived from an organic acid selected from the group consisting of p-toluenesulfonic acid, naphthalenesulphonic acid, naphthalene disulphonic acid, methanesulphonic acid, ethanesulphonic acid and trifluoroacetic acid.

6. The compound of claim 5, wherein the acid addition salt is derived from trifluoroacetic acid.

7. A pharmaceutical composition comprising an effective amount of the compound as claimed in claim 1, and one or more pharmaceutically acceptable excipients.

8. The pharmaceutical composition as claimed in claim 7, wherein the pharmaceutically acceptable excipients are selected from the group consisting of carriers, fillers, binders, disintegrating agents, lubricants, absorbents, wetting agents, buffering agents and a combination thereof.

9. The pharmaceutical composition as claimed in claim 8, wherein the carriers are selected from the group consisting of dicalcium phosphate and sodium citrate.

10. The pharmaceutical composition as claimed in claim 8, wherein the fillers are selected from the group consisting of mannitol, glucose, lactose and sucrose.

11. The pharmaceutical composition as claimed in claim 8, wherein the binders are selected from the group consisting of disaccharides, polysaccharides, sugar alcohols and polymers.

12. The pharmaceutical composition as claimed in claim 11, wherein the disaccharides are selected from the group consisting of sucrose and lactose; the polysaccharides are selected from the group consisting of starch and cellulose the sugar alcohol is sorbitol; and the polymer is polyvinyl pyrrolidinone.

13. The pharmaceutical composition as claimed in claim 8, wherein the disintegrating agents are selected from the group consisting of silicates, agar-agar, and sodium carbonate.

14. The pharmaceutical composition as claimed in claim 8, wherein the lubricants are selected from the group consisting of silica, talc, magnesium stearate, sodium lauryl sulfate and stearic acid.

15. The pharmaceutical composition as claimed in claim 8, wherein the absorbents are selected from the group consisting of bentonite, fuller's earth and kaolin.

16. The pharmaceutical composition as claimed in claim 8, wherein the wetting agents are selected from the group consisting of glycerol monostearate and sodium lauryl sulphate.

\* \* \* \* \*